(12) United States Patent
Gross et al.

(10) Patent No.: US 7,393,367 B2
(45) Date of Patent: Jul. 1, 2008

(54) AGENT FOR DYEING KERATIN-BASED FIBERS

(75) Inventors: Wibke Gross, Dusseldorf (DE); Horst Hoffkes, Dusseldorf (DE); Doris Oberkobusch, Dusseldorf (DE); Helmut Muller, Dusseldorf (DE); Carsten Brake, Mulheim a.d. Ruhr (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 11/937,464

(22) Filed: Nov. 8, 2007

(65) Prior Publication Data

US 2008/0104772 A1    May 8, 2008

Related U.S. Application Data

(63) Continuation of application No. PCT/EP2006/002707, filed on Mar. 24, 2006.

(30) Foreign Application Priority Data

May 12, 2005   (DE) .................. 10 2005 022 790

(51) Int. Cl.
*A61Q 5/10* (2006.01)
*C07D 239/00* (2006.01)

(52) U.S. Cl. ................. 8/405; 8/406; 8/407; 8/410; 8/435; 8/565; 8/567; 8/573; 8/608; 8/613; 544/245

(58) Field of Classification Search ........... 8/405, 8/406, 407, 410, 435, 565, 567, 573, 608, 8/613; 544/245
See application file for complete search history.

(56) References Cited

U.S. PATENT DOCUMENTS

| | | | |
|---|---|---|---|
| 4,865,774 A | 9/1989 | Fabry et al. | |
| 4,931,218 A | 6/1990 | Schenker et al. | |
| 5,061,289 A | 10/1991 | Clausen et al. | |
| 5,294,726 A | 3/1994 | Behler et al. | |
| 5,380,340 A | 1/1995 | Neunhoffer et al. | |
| 5,415,854 A * | 5/1995 | Forestier et al. | 424/59 |
| 5,534,267 A | 7/1996 | Neunhoffer et al. | |
| 5,766,576 A | 6/1998 | Lowe et al. | |
| 6,099,592 A | 8/2000 | Vidal et al. | |
| 6,284,003 B1 | 9/2001 | Rose et al. | |
| 7,105,032 B2 | 9/2006 | Gross et al. | |

FOREIGN PATENT DOCUMENTS

| | | |
|---|---|---|
| DE | 2359399 | 6/1975 |
| DE | 3723354 | 1/1989 |
| DE | 3725030 | 2/1989 |
| DE | 3843892 | 6/1990 |
| DE | 3926344 | 2/1991 |
| DE | 4133957 | 4/1993 |
| DE | 19543988 | 5/1997 |
| DE | 10241076 | 3/2004 |
| EP | 0740931 | 11/1996 |
| EP | 0988908 | 5/2000 |
| GB | 1026978 | 4/1966 |
| GB | 1153196 | 5/1969 |
| JP | 2019576 | 1/1990 |
| WO | WO9408969 | 4/1994 |
| WO | WO9408970 | 4/1994 |
| WO | WO9615765 | 5/1996 |
| WO | WO2004022016 | 3/2004 |
| WO | WO2006029687 | 3/2006 |

OTHER PUBLICATIONS

STIC Search Report dated Mar. 24, 2008.*
H. Moehrle et al., Zum Identitätsnachweis von Coffein im Arzneibuch, 2. Mitt.: Struktur des Farbstoffs aus modifizierter Reaktion Pharmazie, Die, Govi Verlag, Eschborn, DE, Bd. 54 Nr. 4, (1999), Seiten 269-279.
H. Baumann et al., Reaktionen der Methylenebasen von Oxazolidinonen und Pyrimidonen Justus Liebigs Annalen der Chemie, Verlag Chemie GmbH, Weinheim, DE, Bd. 717, (1968), pp. 124-136.
C. Zviak, The Science of Hair Care, Chapter 7 pp. 248-250 and Chapter 8 pp. 264-267 Marcel Dekker, Inc. New York and Basel, (1986).

* cited by examiner

*Primary Examiner*—Eisa B Elhilo
(74) *Attorney, Agent, or Firm*—John E. Drach

(57) ABSTRACT

An agent for dyeing keratin-containing fibers, especially human hair, is comprised of a cosmetic carrier, and
(A) at least one compound of Formula I, $$\text{(I)}$$

[structure: benzene ring with CHO at top, R2 and R3 ortho to CHO, R1 meta, OH at bottom, and an allyl group (-CH_2-CH=CH_2) ortho to OH]

wherein each of $R^1$, $R^2$ and $R^3$ is independently a hydrogen atom, a halogen atom, a $C_1$-$C_6$ alkyl group, a $C_2$-$C_6$ alkenyl group, a hydroxyl group, a $C_1$-$C_6$ alkoxy group, a $C_1$-$C_6$ hydroxyalkyl group, a $C_2$-$C_6$ polyhydroxyalkyl group, a hydroxy $C_1$-$C_6$ alkyloxy group, a sulfonyl group, a carboxyl group, a $C_1$-$C_6$ alkoxycarbonyl group, a hydroxy $C_2$-$C_6$ alkyloxycarbonyl group, a sulfonic acid group, a sulfonamido group, a sulfonamide group, a $C_2$-$C_6$ acyl group, a formyl group, a nitro group, a carbamoyl group —C(O)—$NR^4R^5$, or a —$(CH_2)_n NR^6R^7$ group wherein each of $R^4$, $R^5$, $R^6$ and $R^7$ is independently a hydrogen atom, a $C_1$-$C_6$ alkyl group or a $C_2$-$C_6$ hydroxyalkyl group; and n is number from 0 to 6, wherein $R^1$ and $R^2$ can form a 5- or 6-membered aromatic or heteroaromatic ring; and (B) at least one CH-acidic compound.

22 Claims, No Drawings

AGENT FOR DYEING KERATIN-BASED FIBERS

CROSS-REFERENCE TO RELATED APPLICATIONS

This application is a continuation under 35 U.S.C. § 365(c) and 35 U.S.C. § 120 of International Application No. PCT/EP2006/002707, filed Mar. 24, 2006. This application also claims priority under 35 U.S.C. § 119 of German Patent Application No. DE 10 2005 022 790.2, filed May 12, 2005. Both the International Application and the German Application are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to an agent for dyeing keratin-based fibers, particularly human hair, which comprises 3-allyl-4-hydroxybenzaldehyde and/or its derivatives in combination with CH-acidic compounds, the use of this combination in agents for dyeing keratin-containing fibers, for refreshing the color or nuancing previously colored keratin-containing fibers as well as a method for dyeing keratin-containing fibers, in particular, human hair.

Generally, either substantive dyes or oxidation dyes that result from oxidative coupling of one or more developer components with each other or with one or more coupler components are used for coloring fibers containing keratin. Coupler components and developer components are also called oxidation dye precursors.

Normally, primary aromatic amines with an additional free or substituted hydroxyl or amino group in the para or ortho position, diaminopyridine derivatives, heterocyclic hydrazones, 4-amino pyrazole derivatives as well as 2,4,5,6-tetramino pyrimidine and derivatives thereof are employed as the developer components.

Specific exemplary representatives are p-phenylenediamine, p-toluenediamine, 2,4,5,6-tetraminopyrimidine, p-aminophenol, N,N-bis(2-hydroxyethyl)-p-phenylenediamine, 2-(2,5-diaminophenyl)-ethanol, 2-(2,5-diaminophenoxy)ethanol, 1-phenyl-3-carboxyamido-4-amino-pyrazolone-5,4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

m-Phenylenediamine derivatives, naphthols, resorcinol and resorcinol derivatives, pyrazolones, m-aminophenols and substituted pyridine derivatives are generally used as the coupling components. Particularly suitable coupling substances are α-naphthol, 1,5-dihydroxynaphthalene, 2,7-dihydroxynaphthalene and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino) anisole (Lehmann's Blue), 1-phenyl-3-methylpyrazolone-5, 2,4-dichloro-3-aminophenol, 1,3-bis(2',4'-diaminophenoxy) propane, 2-chloro resorcinol, 4-chloro resorcinol, 2-chloro-6-methyl-3-aminophenol, 2-methyl resorcinol, 5-methyl resorcinol, 3-amino-6-methoxy-2-methylaminopyridine and 3,5-diamino-2,6-dimethoxypyridine.

(2) Description of Related Art, Including Information Disclosed Under 37 C.F.R. §§ 1.97 and 1.98

In regard to further typical dye components, reference is expressly made to the series "Dermatology", edited by Ch. Culnan and H. Maibach, Verlag Marcel Dekker Inc., New York, Basel, 1986, volume 7, Ch. Zviak, The Science of Hair Care, chapter 7, pages 248-250 (substantive dyes), and chapter 8, pages 264-267 (oxidation dyes), as well as the "European Inventory of Cosmetic Raw Materials", published by the European Union, obtainable in disk form from the Bundesverband Deutscher Industrie-und Handelsunternehmen für Arzneimittel, Reformwaren und Körperpflegemittel e.V., Mannheim.

Indeed, with the oxidation dyes, intensive colorations can be achieved with good fastness characteristics, but the development of the color normally occurs in the presence of oxidizing agents such as, for example $H_2O_2$, which in some cases can result in damage to the fibers. It still proves problematic to prepare oxidative hair colorations in the red tones having adequate fastness characteristics, especially with very good wash fastness and rubbing fastness. Furthermore, some of the oxidation dye precursors or certain mixtures of oxidation dye precursors sometimes have a sensitizing effect on people with delicate skin. The substantive dyes are applied under more gentle conditions, but their disadvantage is that the resulting colorations often possess only inadequate fastness characteristics.

The object of the present invention is to provide dyes for fibers containing keratin, especially human hair, which in regard to the color depth and fastness characteristics, such as for example light fastness, rubbing fastness and wash fastness as well as fastness to perspiration and to cold waving, are qualitatively at least equivalent to the conventional oxidation hair dyes, without, however being necessarily dependent on oxidizing agents such as for example $H_2O_2$. Furthermore, the dyes must have no or only a very slight sensitization potential and in no case may have a mutagenic effect. Dyes, comprising 3-allyl-4-hydroxybenzaldehyde and its derivatives according to the following Formula I in combination with CH-acidic compounds, as well as the use of this combination for dyeing fibers containing keratin or for color refreshing or nuancing already dyed fibers containing keratin, are unknown up to now.

CH-acidic 1,2-dihydropyrimidinium derivatives, which are known from the patent application WO A1 2004/022016, when combined with reactive carbonyl compounds, particularly benzaldehyde derivatives, are suitable for dyeing keratin-containing fibers. However, 3-allyl-4-hydroxybenzaldehyde and its derivatives in accordance with the present invention are not mentioned.

BRIEF SUMMARY OF THE INVENTION

Surprisingly, it has now been found that the compounds illustrated in Formula I in combination with CH-acidic compounds are eminently suitable, even in the absence of oxidizing agents, for dyeing fibers containing keratin. They produce colorations with excellent brilliance and depth of color and lead to a wide range of color nuances. In particular, colorations are obtained with improved fastness characteristics over a range of nuances from yellow through orange, brown orange, brown, red, red-violet up to blue-violet and dark blue.

However, in principle the use of oxidizing agents should not be excluded. Moreover, the inventive benzaldehyde derivatives are characterized by an increased physiological compatibility.

One aspect of the invention pertains to an agent for dyeing keratin-containing fibers, especially human hair, comprising a cosmetic carrier, and (A) at least one compound of Formula I,

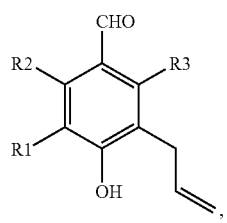

wherein each of $R^1$, $R^2$ and $R^3$ is independently a hydrogen atom, a halogen atom, a $C_1$-$C_6$ alkyl group, a $C_2$-$C_6$ alkenyl group, a hydroxyl group, a $C_1$-$C_6$ alkoxy group, a $C_1$-$C_6$ hydroxyalkyl group, a $C_2$-$C_6$ polyhydroxyalkyl group, a hydroxy $C_1$-$C_6$ alkyloxy group, a sulfonyl group, a carboxyl group, a $C_1$-$C_6$ alkoxycarbonyl group, a hydroxy $C_2$-$C_6$ alkoxycarbonyl group, a sulfonic acid group, a sulfonamido group, a sulfonamide group, a $C_2$-$C_6$ acyl group, a formyl group, a nitro group, a carbamoyl group —C(O)—$NR^4R^5$, or a —$(CH_2)_n NR^6R^7$ group wherein each of $R^4, R^5, R^6$ and $R^7$ is independently a hydrogen atom, a $C_1$-$C_6$ alkyl group or a $C_2$-$C_6$ hydroxyalkyl group; and n is a number from 0 to 6, wherein $R^1$ and $R^2$ can form a 5- or 6-membered aromatic or heteroaromatic ring; and (B) at least one CH-acidic compound.

BRIEF DESCRIPTION OF THE SEVERAL VIEWS OF THE DRAWING(S)

Not Applicable

DETAILED DESCRIPTION OF THE INVENTION

Keratin-containing fibers are understood to mean wool, furs, feathers and particularly human hair. However, the inventive dyes can, in principle, also be used for dyeing other natural fibers, such as e.g., cotton, jute, sisal, linen or silk, modified natural fibers, such as e.g., cellulose regenerate, nitrocellulose, alkyl cellulose or hydroxyalkyl cellulose or acetyl cellulose.

Examples of $C_1$-$C_6$ alkyl groups are the methyl, ethyl, propyl, isopropyl, n-butyl, sec-butyl and tert.-butyl, n-pentyl and n-hexyl groups. Propyl, ethyl and methyl are preferred alkyl groups. Examples of suitable cyclic alkyl groups are cyclopentyl and cyclohexyl groups. Examples of preferred $C_2$-$C_6$ alkenyl groups are vinyl and allyl groups.

Furthermore, preferred examples of a $C_1$-$C_6$ hydroxyalkyl group can be a hydroxymethyl, a 2-hydroxyethyl, a 2-hydroxypropyl, a 3-hydroxypropyl, a 4-hydroxybutyl group, a 5-hydroxypentyl and a 6-hydroxyethyl group. A 2-hydroxyethyl group is particularly preferred.

Examples of a $C_2$-$C_6$ polyhydroxyalkyl group are the 2,3-dihydroxypropyl group, 3,4-dihydroxybutyl group and the 2,4-dihydroxybutyl group.

Inventively preferred $C_1$-$C_6$ alkoxy groups are a methoxy or ethoxy group, for example.

The methoxycarbonyl, ethoxycarbonyl, n-propoxycarbonyl, isopropoxycarbonyl, n-butoxycarbonyl, sec-butoxycarbonyl, tert-butoxycarbonyl groups, n-pentyloxycarbonyl and n-hexyloxycarbonyl are examples of $C_1$-$C_6$ alkoxycarbonyl groups; the methoxycarbonyl and the ethoxycarbonyl groups are particularly preferred.

The acetyl, n-propanoyl, n-butanoyl groups and n-hexanoyl groups are examples of a $C_2$-$C_6$ acyl group.

The methoxyethyl, ethoxyethyl, methoxypropyl, methoxybutyl, ethoxybutyl and the methoxyhexyl group are examples of the inventive $C_1$-$C_6$ alkoxy $C_2$-$C_6$ alkyl groups.

A preferred hydroxy ($C_1$-$C_6$) alkoxy group is the 2-hydroxyethoxy group.

A preferred hydroxy ($C_2$-$C_6$) alkoxycarbonyl group is the 2-hydroxyethoxycarbonyl group.

Exemplary halogen atoms are F, Cl, Br or I atoms, Cl atoms being quite particularly preferred.

The aminomethyl, 2-aminoethyl, 3-aminopropyl, 2-dimethylaminoethyl, diethylaminomethyl, dimethylaminomethyl, 2-methylaminoethyl, dimethylamino, piperidinomethyl, pyrrolidinomethyl, morpholinomethyl, bis(2-hydroxyethyl)amino and the amino group are examples of a $R^6R^7N$—$(CH_2)_n$— group, wherein the diethylaminomethyl, piperidinomethyl, 2-dimethylaminoethyl, dimethylamino and the amino group are particularly preferred.

The N,N-dimethylcarbamoyl, N,N-diethylcarbamoyl, N,N-bis(2-hydroxyethyl)carbamoyl and the carbamoyl group are exemplary carbamoyl groups $R^4R^5NC(O)$—. The other terms used are derived according to the invention from the definitions given here.

In a preferred embodiment, the inventive composition comprises at least one compound according to Formula (I), which carry a hydrogen atom as the substituent $R^2$ and $R^3$. Furthermore, representatives of the compounds corresponding to Formula (I) are preferred, in which the $R^1$ group carries a hydrogen atom, a $C_1$-$C_6$ alkyl group, a $C_2$-$C_6$ alkenyl group (especially an allyl group), a $C_1$-$C_6$ alkoxy group (especially a methoxy group), a formyl group, a hydroxyl group, a halogen atom, a carboxy group or a nitro group. Once again, in this embodiment, the groups $R^2$ and $R^3$ particularly preferably stand for a hydrogen atom.

It is particularly preferred if at least one of the following compounds corresponding to Formula (I) is comprised in the inventive composition:
3-Allyl-4-hydroxybenzaldehyde,
3-Allyl-4-hydroxy-5-methoxybenzaldehyde,
3-Allyl-5-ethoxy-4-hydroxybenzaldehyde,
3-Allyl-4-hydroxy-5-methylbenzaldehyde,
3-Allyl-5-bromo-4-hydroxybenzaldehyde,
3,5-Diallyl-4-hydroxybenzaldehyde,
3-Allyl-4,5-dihydroxybenzaldehyde,
3-Allyl-4-hydroxy-5-nitrobenzaldehyde,
3-Allyl-5-carboxy-4-hydroxybenzaldehyde    (3-allyl-5-formyl-2-hydroxybenzoic acid),
3-Allyl-4-hydroxy-5-formylbenzaldehyde    (5-allyl-4-hydroxyisophthalaldehyde).

Quite particularly preferably, the inventive compositions comprise at least one compound from the group
3-Allyl-4-hydroxybenzaldehyde,
3-Allyl-4-hydroxy-5-methoxybenzaldehyde,
3-Allyl-4-hydroxy-5-methylbenzaldehyde,
3-Allyl-5-bromo-4-hydroxybenzaldehyde,
3,5-Diallyl-4-hydroxybenzaldehyde,
3-Allyl-5-carboxy-4-hydroxybenzaldehyde    (3-allyl-5-formyl-2-hydroxybenzoic acid),
3-Allyl-4-hydroxy-5-formylbenzaldehyde    (5-allyl-4-hydroxyisophthalaldehyde).

Moreover, according to the invention, such compounds corresponding to Formula (I) can also be used as Component A, in which the reactive carbonyl group is protected or derivatized in such a manner that the carbon atom of the derivatized carbonyl group is still reactive towards the CH-acidic compounds of the compound B. These derivatives are preferably addition compounds a) of amines and their derivatives forming imines or oximes as the addition compound
b) of alcohols forming acetals as the addition compound
c) of water, forming hydrates as the addition compound onto the carbon atom of the formyl group —CHO in compounds corresponding to Formula (I).

In general, those compounds that possess a hydrogen atom bonded to an aliphatic carbon atom, wherein the carbon-hydrogen bond is activated due to electron-withdrawing substituents, are recognized as CH-acidic compounds. In principle there are no limits to the choice of the CH-acidic compounds, as long as a compound that is colored to the human eye is obtained after the aldol condensation with the inventive benzaldehyde derivatives of Formula (I). According to the invention, they are preferably CH-acidic compounds that comprise an aromatic and/or a heterocyclic group. Once again, the heterocyclic group can be aliphatic or aromatic in nature.

The 3-allyl-4-hydroxybenzaldehyde compounds of Formula (I) combined with at least one CH-acidic compound selected from Formulas (II) and/or (III) are preferred

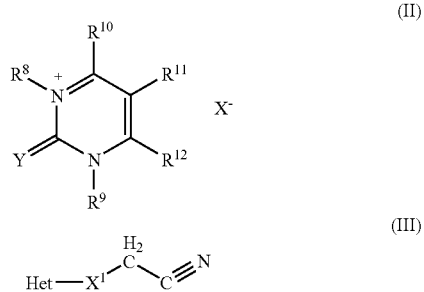

in which
$R^8$ and $R^9$ independently of one another stand for a linear or cyclic $C_1$-$C_6$ alkyl group, a $C_2$-$C_6$ alkenyl group, an optionally substituted aryl group, an optionally substituted heteroaryl group, an aryl $C_1$-$C_6$ alkyl group, a $C_1$-$C_6$ hydroxyalkyl group, a $C_2$-$C_6$ polyhydroxyalkyl group, a $C_1$-$C_6$ alkoxy $C_1$-$C_6$ alkyl group, a $R^I R^{II} N$—$(CH_2)_m$— group, in which $R^I$ and $R^{II}$ stand independently of one another for a hydrogen atom, a $C_1$-$C_4$ alkyl group, a $C_1$-$C_4$ hydroxyalkyl group or an aryl $C_1$-$C_6$ alkyl group, wherein $R^I$ and $R^{II}$ together with the nitrogen atom can form a 5-, 6- or 7-membered ring and m stands for a number 2, 3, 4, 5 or 6, $R^{10}$ and $R^{12}$ independently of one another stand for a hydrogen atom or a $C_1$-$C_6$ alkyl group, wherein at least one of the groups $R^{10}$ and $R^{12}$ means a $C_1$-$C_6$ alkyl group, $R^{11}$ stands for a hydrogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, a $R^{III} R^{IV} N$—$(CH_2)_q$— group, in which $R^{III}$ and $R^{IV}$ independently of one another stand for a hydrogen atom, a $C_1$-$C_6$ alkyl group, a $C_1$-$C_6$ hydroxyalkyl group or an aryl $C_1$-$C_6$ alkyl group and q stands for a number 1, 2, 3, 4, 5 or 6, wherein the group $R^{11}$ together with one of the groups $R^{10}$ or $R^{12}$ can form a 5- or 6-membered aromatic ring that can be optionally substituted with a halogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, a nitro group, a hydroxy group, a $R^V R^{VI} N$—$(CH_2)_s$— group, in which $R^V$ and $R^{VI}$ independently of one another stand for a hydrogen atom, a $C_1$-$C_6$ alkyl group, a $C_1$-$C_6$ hydroxyalkyl group or an aryl $C_1$-$C_6$ alkyl group and s stands for a number 0, 1, 2, 3, 4, 5 or 6, Y stands for an oxygen atom, a sulfur atom or a group $NR^{VII}$, in which $R^{VII}$ stands for a hydrogen atom, an aryl group, a heteroaryl group, a $C_1$-$C_6$ alkyl group or a $C_1$-$C_6$ arylalkyl group, $X^-$ stands for a physiologically compatible anion, Het stands for an optionally substituted heteroaromatic group, $X^1$ stands for a direct bond or a carbonyl group.

The enamine forms act in the same way as the compounds of Formula II. Here, reference is expressly made to the publication WO A1 2004/022016, which is incorporated in its entirety.

At least one group $R^{10}$ or $R^{12}$ of Formula II stands imperatively for a $C_1$-$C_6$ alkyl group. This alkyl group preferably carries at least two hydrogen atoms on its α-carbon atom. Particularly preferred alkyl groups are the methyl-, ethyl-, propyl-, n-butyl-, iso-butyl, n-pentyl-, neo-pentyl-, n-hexyl groups. $R^{10}$ and $R^{12}$ independently of one another stand quite particularly preferably for hydrogen or a methyl group, wherein at least one of the groups $R^{10}$ or $R^{12}$ means a methyl group.

In a preferred embodiment, Y stands for an oxygen atom or a sulfur atom, particularly preferably for an oxygen atom.

The group $R^8$ is preferably selected from a $(C_1$-$C_6)$ alkyl group (particularly preferably a methyl group), a $C_2$-$C_6$ alkenyl group (especially an allyl group), a hydroxy $(C_2$- to $C_6)$ alkyl group or an optionally substituted benzyl group.

$R^{11}$ preferably stands for a hydrogen atom.

The groups $R^9$, $R^{10}$ und $R^{12}$ particularly preferably stand for a methyl group, the group $R^{11}$ for a hydrogen atom, Y for an oxygen atom or a sulfur atom and the group $R^8$ is selected from a $(C_1$-$C_6)$ alkyl group (particularly preferably a methyl group), a $C_2$-$C_6$ alkenyl group (especially an allyl group), a hydroxy $(C_2$- to $C_6)$ alkyl group or an optionally substituted benzyl group.

Preferably, the compounds according to Formula II are selected from one or a plurality of compounds of the group of salts with physiologically compatible counter ions $X^-$, said group being formed from salts of 1,2-Dihydro-1,3,4,6-tetramethyl-2-oxo-pyrimidinium,
1,2-Dihydro-1,3-diethyl-4,6-dimethyl-2-oxo-pyrimidinium,
1,2-Dihydro-1,3-dipropyl-4,6-dimethyl-2-oxo-pyrimidinium,
1,2-Dihydro-1,3-di(2-hydroxyethyl)-4,6-dimethyl-2-oxo-pyrimidinium,
1,2-Dihydro-1,3-diphenyl-4,6-dimethyl-2-oxo-pyrimidinium,
1,2-Dihydro-1,3,4-trimethyl-2-oxo-pyrimidinium,
1,2-Dihydro-1,3-diethyl-4-methyl-2-oxo-pyrimidinium,
1,2-Dihydro-1,3-dipropyl-4-methyl-2-oxo-pyrimidinium,
1,2-Dihydro-1,3-di(2-hydroxyethyl)-4-methyl-2-oxo-pyrimidinium
1,2-Dihydro-1,3-diphenyl-4-methyl-2-oxo-pyrimidinium,
1-Allyl-1,2-dihydro-3,4,6-trimethyl-2-oxo-pyrimidinium,
1,2-Dihydro-1-(2-hydroxyethyl)-3,4,6-trimethyl-2-oxo-pyrimidinium, 1,2-Dihydro-1,3,4,6-tetramethyl-2-thioxo-pyrimidinium,
1,2-Dihydro-1,3-diethyl-4,6-dimethyl-2-thioxo-pyrimidinium,
1,2-Dihydro-1,3-dipropyl-4,6-dimethyl-2-thioxo-pyrimidinium,
1,2-Dihydro-1,3-di(2-hydroxyethyl)-4,6-dimethyl-2-thioxo-pyrimidinium,
1,2-Dihydro-1,3-diphenyl-4,6-dimethyl-2-thioxo-pyrimidinium,
1,2-Dihydro-1,3,4-trimethyl-2-thioxo-pyrimidinium,
1,2-Dihydro-1,3-diethyl-4-methyl-2-thioxo-pyrimidinium,
1,2-Dihydro-1,3-dipropyl-4-methyl-2-thioxo-pyrimidinium,
1,2-Dihydro-1,3-di(2-hydroxyethyl)-4-methyl-2-thioxo-pyrimidinium,
1,2-Dihydro-1,3-diphenyl-4-methyl-2-thioxo-pyrimidinium,
1,2-Dihydro-3,4-dimethyl-2-oxo-quinazolinium and
1,2-Dihydro-3,4-dimethyl-2-thioxo-quinazolinium.

Quite particularly preferable compounds according to Formula II are selected from one or a plurality of compounds of the group of salts with physiologically compatible counter ions X⁻, said group being formed from salts of
1,2-Dihydro-1,3,4,6-tetramethyl-2-oxo-pyrimidinium,
1,2-Dihydro-1,3,4-trimethyl-2-oxo-pyrimidinium,
1-Allyl-1,2-dihydro-3,4,6-trimethyl-2-oxo-pyrimidinium,
1,2-Dihydro-1-(2-hydroxyethyl)-3,4,6-trimethyl-2-oxo-pyrimidinium and
1,2-Dihydro-1,3,4,6-tetramethyl-2-thioxo-pyrimidinium.

$X^-$ in Formula (II) as well as in the above lists preferably stands for halide, benzenesulfonate, p-toluenesulfonate, $C_1$-$C_4$ alkanesulfonate, trifluoromethanesulfonate, perchlorate, 0.5 sulfate, hydrogen sulfate, tetrafluoroborate, hexafluorophosphate or tetrachlorozincate. The anions chloride, bromide, iodide, hydrogen sulfate or p-toluenesulfonate are particularly preferably employed as $X^-$.

The group Het according to Formula (III) preferably stands for the molecule fragment with the following Formula (IV),

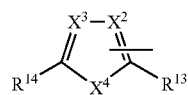

(IV)

in which
$R^{13}$ and $R^{14}$ stand independently of one another for a hydrogen atom, a hydroxyl group, a halogen atom, a nitro group, a linear or cyclic $C_1$-$C_6$ alkyl group, a $C_2$-$C_6$ alkenyl group, an optionally substituted aryl group, a cyanomethyl group, a cyanomethyl carbonyl group, an optionally substituted heteroaryl group, an aryl $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ alkoxycarbonyl group, a $C_1$-$C_6$ alkoxy $C_2$-$C_6$ alkyl group, a $C_1$-$C_6$ sulfoalkyl group, a $C_1$-$C_6$ carboxyalkyl group, a $R^{VIII}R^{IX}N-(CH_2)_m-$ group, in which $R^{VIII}$ and $R^{IX}$ stand independently of one another for a hydrogen atom, a linear or cyclic $C_1$-$C_6$ alkyl group, a $C_2$-$C_6$ alkenyl group, a $C_1$-$C_6$ hydroxyalkyl group or an aryl $C_1$-$C_4$ alkyl group, wherein $R^{VIII}$ and $R^{IX}$ together with the nitrogen atom can form a 5-, 6- or 7-membered ring and m stands for a number 0, 1, 2, 3 or 4,
wherein $R^{13}$ and/or $R^{14}$ can form an annulated, optionally substituted aromatic or heteroaromatic 5- or 6-membered ring on the ring of the residual molecule $X^2$ and $X^3$ stand independently of one another for a nitrogen atom or a $CR^{15}$ group, wherein $R^{15}$ stands for a hydrogen atom, a hydroxyl group, a halogen atom, a nitro group, a linear or cyclic $C_1$-$C_6$ alkyl group, a $C_2$-$C_6$ alkenyl group, an optionally substituted aryl group, a cyanomethyl group, a cyanomethyl carbonyl group, an optionally substituted heteroaryl group, an aryl $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ alkoxycarbonyl group, a $C_1$-$C_6$ alkoxy $C_2$-$C_6$ alkyl group, a $C_1$-$C_6$ sulfoalkyl group, a $C_1$-$C_6$ carboxyalkyl group and a $R^{X}R^{XI}N-(CH_2)_n-$ group, in which $R^{X}$ and $R^{XI}$ stand independently of one another for a hydrogen atom, a linear or cyclic $C_1$-$C_6$ alkyl group, a $C_2$-$C_6$ alkenyl group, a $C_1$-$C_6$ hydroxyalkyl group or an aryl $C_1$-$C_4$ alkyl group, wherein $R^{X}$ and $R^{XI}$ together with the nitrogen atom can form a 5-, 6- or 7-membered ring and n stands for a number 0, 1, 2, 3 or 4,
wherein at least one of the substituents $X^2$ and $X^3$ can form an annulated, optionally substituted aromatic 5- or 6-membered ring together with the residual molecule,
$X^4$ stands for an oxygen atom, a sulfur atom, a vinylene group or an N—H group, wherein the last two groups, independently of one another, can be optionally substituted with a linear or cyclic $C_1$-$C_6$ alkyl group, a $C_2$-$C_6$ alkenyl group, an optionally substituted aryl group, an optionally substituted heteroaryl group, an aryl $C_1$-$C_6$ alkyl group, a $C_2$-$C_6$ hydroxyalkyl group, a $C_2$-$C_6$ polyhydroxyalkyl group, a $C_1$-$C_6$ alkoxy $C_2$-$C_6$ alkyl group, a $C_1$-$C_6$ sulfoalkyl group, a $C_1$-$C_6$ carboxyalkyl group, a group $R^{XII}R^{XIII}N-(CH_2)_p-$, in which $R^{XII}$ and $R^{XIII}$ stand independently of one another for a hydrogen atom, a linear or cyclic $C_1$-$C_6$ alkyl group, a $C_2$-$C_6$ alkenyl group, a $C_1$-$C_6$ hydroxyalkyl group or an aryl $C_1$-$C_4$ alkyl group, wherein $R^{XII}$ and $R^{XIII}$ together with the nitrogen atom can form a 5-, 6- or 7-membered ring and p stands for a number 0, 1, 2, 3 or 4, with the proviso that when $X^4$ stands for a vinylene group, at least one of the groups $X^2$ or $X^3$ means a nitrogen atom.

The bond between the heterocyclic ring of Formula (IV) and the molecule fragment $-X^1-CH_2-C\equiv N$ with retention of the inventive compound of Formula (III) occurs on the ring of the heterocycle and substitutes a hydrogen atom bonded to this ring. Consequently, it is imperative that the substituents $R^{13}$, $R^{14}$, $X^2$, $X^3$ and $X^4$ are selected such that at least one of these substituents permits the formation of a corresponding bond. Consequently, it is imperative that at least one of the groups $R^{13}$ or $R^{14}$ forms the bond to the molecule fragment $-X^1-CH_2-C\equiv N$, when $X^4$ is an oxygen atom or a sulfur atom and $X^2$ and $X^3$ mean a nitrogen atom.

The group Het of Formula (IV) is particularly preferably derived from the heteroaromatics furan, thiophene, pyrrole, isoxazole, isothiazole, imidazole, oxazole, thiazole, pyridine, pyridazine, pyrimidine, pyrazine, 1,2,3-triazine, 1,2,4-triazine, 1,3,5-triazine, benzopyrrole, benzofuran, benzothiophene, benzimidazole, benzoxazole, indazole, benzoisoxazole, benzoisothiazole, indole, quinoline, isoquinoline, cinnolin, phthalazine, quinazoline, quinoxaline, acridine, benzoquinoline, benzoisoquinoline, benzothiazole, phenazine, benzocinnolin, benzoquinazoline, benzoquinoxaline, phenoxazine, phenothiazine, nephthyridine, phenanthroline, indolizine, quinolizine, carboline, purine, pteridine and cumarine, wherein the above-cited heteroaromatics can be substituted with at least one group selected from a halogen atom, a nitro group, a thio group, a thio (C₁-C₆) alkyl group, a heteroaryl group, an aryl group, a (C₁-C₆) alkyl group, a (C₁-C₆) alkoxy group, a hydroxy group, a (C₂-C₆) hydroxyalkyl group, a (C₂-C₆) polyhydroxyalkyl group, a (C₁-C₆) alkoxy (C₁-C₆) alkyl group, an aryl (C₁-C₆) alkyl group, an amino group, a (C₁-C₆) monoalkylamino group, a (C₁-C₆) dialkylamino group, a dialkylaminoalkyl group —(CH₂)ₙ—NR'R'', in which n is a whole number from 2 and 6 and R' and R'' independently of one another means a linear or branched alkyl group that can together optionally form a ring.

The compounds according to Formula (III) are advantageously selected from the group consisting of 2-(2-furoyl)-acetonitrile, 2-(5-bromo-2-furoyl)-acetonitrile, 2-(5-methyl-2-trifluormethyl-3-furoyl)-acetonitrile, 3-(2,5-dimethyl-3-furyl)-3-oxopropanitrile, 2-(2-thenoyl)-acetonitrile, 2-(3-thenoyl)-acetonitrile, 2-(5-fluoro-2-thenoyl)-acetonitrile, 2-(5-chloro-2-thenoyl)-acetonitrile, 2-(5-bromo-2-thenoyl)-acetonitrile, 2-(5-methyl-2-thenoyl)-acetonitrile, 2-(2,5-dimethylpyrrol-3-oyl)-acetonitrile, 2-(1,2,5-trimethylpyrrol-3-oyl)-acetonitrile, 1H-benzimidazol-2-ylacetonitrile, 1H-benzothiazol-2-ylacetonitrile, 2-(pyrid-2-yl)-acetonitrile, 2,6-bis(cyanomethyl)-pyridine, 2-(indol-3-oyl)-acetonitrile, 2-(2-methyl-indol-3-oyl)-acetonitrile, 8-cyanoacetyl-7-methoxy-4-methylcumarine, 2-(2-isopropyl-5,6-benzoquinolin-4-oyl)-acetonitrile, 2-(2-phenyl-5,6-benzoquinolin-4-oyl)-acetonitrile, 2-(quinoxalin-2-yl)-acetonitrile, 2-(cumaron-2-yl)-acetonitrile, 6,7-dichloro-5-(cyanoacetyl)-2,3-dihydro-1-benzofuran-2-carboxylic acid tert.-butyl ester, 2-(6-hydroxy-4,7-dimethoxy-1-benzofuran-5-oyl)-acetonitrile and 2-(1-phenyl-1,4-dihydrothiochromeno[4,3-c]pyrazol-3-oyl)-acetonitrile. 1H-Benzimidazol-2-yl acetonitrile [2-(cyanomethyl)benzimidazole] is particularly preferred.

In another aspect of the invention, it can be advantageous for broadening the color spectrum to add at least one further compound as Component C in addition to at least one compound corresponding to Formula (I) as Component A and at least one compound of Component B. The compound of Component C is preferably selected from at least one reactive carbonyl compound that is different from the compounds of Formula (I).

In the context of the invention, reactive carbonyl compounds as Component C possess at least one carbonyl group as the reactive group that reacts with the CH-acidic compound corresponding to Component B to form a carbon-carbon bond. Preferred reactive carbonyl compounds are the aldehydes and ketones, particularly aromatic aldehydes. Moreover, according to the invention, such compounds are also applicable as Component C, in which the reactive carbonyl group is derivatized or protected in such a manner that the reactivity of the carbon atom of the derivatized carbonyl group remains towards the CH-acidic compounds of Component B. These derivatives are preferably addition compounds
a) of amines and their derivatives forming imines or oximes as the addition compounds
b) of alcohols forming acetals or ketals as the addition compounds
c) of water forming hydrates as the addition product (in this case c), Component C is derived from an aldehyde)

on the carbon atom of the carbonyl group of the reactive carbonyl compound.

Preferred reactive carbonyl compounds of Component C are selected from the group consisting of benzaldehyde and its derivatives, naphthaldehyde and its derivatives, cinnamaldehyde and its derivatives, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazol-3-aldehyde, 2-formylmethylene-1,3,3-trimethylindoline (Fischer's aldehyde or tribasic aldehyde),2-indole aldehyde, 3-indole aldehyde, 1-methylindol-3-aldehyde, 2-methylindol-3-aldehyde, 2-(1',3',3'-trimethyl-2-indolinylidene)-acetaldehyde, 1-methylpyrrole-2-aldehyde, 4-pyridine aldehyde, 2-pyridine aldehyde, 3-pyridine aldehyde, pyridoxal, antipyrin-4-aldehyde, furfural, 5-nitrofurfural, 2-thenoyl-trifluoroacetone, chromone-3-aldehyde, 3-(5'-nitro-2'-furyl)-acrolein, 3-(2'-furyl)-acrolein and imidazol-2-aldehyde, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, 9-methyl-3-carbazolaldehyde, 9-ethyl-3-carbazolaldehyde, 3-acetylcarbazole, 3,6-diacetyl-9-ethylcarbazole, 3-acetyl-9-methylcarbazole, 1,4-dimethyl-3-carbazolaldehyde, 1,4,9-trimethyl-3-carbazolaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-formyl-1-methylpyridinium-, 2-formyl-1-methylpyridinium-, 4-formyl-1-ethylpyridinium-, 2-formyl-1-ethylpyridinium-, 4-formyl-1-benzylpyridinium-, 2-formyl-1-benzylpyridinium-, 4-formyl-1,2-dimethylpyridinium-, 4-formyl-1,3-dimethylpyridinium-, 4-formyl-1-methylquinolinium-, 2-formyl-1-methylquinolinium-, 5-formyl-1-methylquinolinium-, 6-formyl-1-methylquinolinium-, 7-formyl-1-methylquinolinium-, 8-formyl-1-methylquinolinium-, 5-formyl-1-ethylquinolinium-, 6-formyl-1-ethylquinolinium-, 7-formyl-1-ethylquinolinium-, 8-formyl-1-ethylquinolinium-, 5-formyl-1-benzylquinolinium-, 6-formyl-1-benzylquinolinium-, 7-formyl-1-benzylquinolinium-, 8-formyl-1-benzylquinolinium-, 5-formyl-1-allylquinolinium-, 6-formyl-1-allylquinolinium-, 7-formyl-1-allylquinolinium- and 8-formyl-1-allylquinolinium benzenesulfonate, -p-toluenesulfonate, -methanesulfonate, -perchlorate, -sulfate, -chloride, -bromide, -iodide, -tetrachlorozincate, -methylsulfate, -trifluoromethanesulfonate, -tetrafluoroborate, isatin, 1-methyl-isatin, 1-allyl-isatin, 1-hydroxymethyl-isatin, 5-chloro-isatin, 5-methoxy-isatin, 5-nitro-isatin, 6-nitro-isatin, 5-sulfo-isatin, 5-carboxy-isatin, quinisatin, 1-methylquinisatin, as well as any mixture of the above compounds.

Benzaldehyde, cinnamaldehyde and naphthaldehyde together with their derivatives, in particular, with one or more hydroxyl, alkoxy or amino substituents, are quite particularly preferred as the reactive carbonyl compound of Component C. Again, the compounds according to Formula (Ca-1) are preferred.

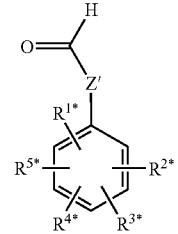

(Ca-1)

in which

R¹*, R²* and R³* independently of each other stand for a hydrogen atom, a halogen atom, a $C_1$-$C_6$ alkyl group, a hydroxyl group, a $C_1$-$C_6$ alkoxy group, a $C_1$-$C_6$ dialkylamino group, a di($C_2$-$C_6$ hydroxyalkyl)amino group, a di($C_1$-$C_6$ alkoxy $C_1$-$C_6$ alkyl)amino group, a $C_1$-$C_6$ hydroxyalkyloxy group, a sulfonyl group, a carboxyl group, a sulfonic acid group, a sulfonamido group, a sulfonamide group, a carbamoyl group, a $C_2$-$C_6$ acyl group or a nitro group, Z' stands for a direct bond or a vinylene group, R⁴* and R⁵* stand for a hydrogen atom or together form a 5- or 6-membered aromatic or aliphatic ring with the rest of the molecule.

The derivatives of benzaldehyde, naphthaldehyde or cinnamaldehyde of the reactive carbonyl compound according to Component C are particularly preferably selected from 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 3,5-diethoxy-4-hydroxy-benzaldehyde, 2,6-diethoxy-4-hydroxy-benzaldehyde, 3-hydroxy-4-methoxy-benzaldehyde, 2-hydroxy-4-methoxy-benzaldehyde, 2-ethoxy-4-hydroxy-benzaldehyde, 3-ethoxy-4-hydroxy-benzaldehyde, 4-ethoxy-2-hydroxy-benzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methyl-benzaldehyde, 2,4-dihydroxy-5-methyl-benzaldehyde, 2,4-dihydroxy-6-methyl-benzaldehyde, 2,4-dihydroxy-3-methoxy-benzaldehyde, 2,4-dihydroxy-5-methoxy-benzaldehyde, 2,4-dihydroxy-6-methoxy-benzaldehyde, 2,5-dihydroxybenzaldehyde, 2,6-dihydroxybenzaldehyde, 3,4-dihydroxybenzaldehyde, 3,4-dihydroxy-2-methyl-benzaldehyde, 3,4-dihydroxy-5-methyl-benzaldehyde, 3,4-dihydroxy-6-methyl-benzaldehyde, 3,4-dihydroxy-2-methoxy-benzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodo-benzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iod-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 4-nitro-1-naphthaldehyde, 2-nitrocinnamaldehyde, 3-nitrocinnamaldehyde, 4-nitrocinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylamino-benzaldehyde, 4-diphenylamino-benzaldehyde, 4-(1-imidazolyl)-benzaldehyde and piperonal. Together, these representatives are the particularly preferred additional reactive carbonyl compounds of Component C.

In another aspect of the invention, the colorant additionally comprises at least one reaction product (hereafter named reaction product RP) as the substantive dye from a compound of Formula (I) and a compound of Component B. These types of reaction products RP can be obtained by e.g., heating both reactants in a neutral to weakly alkaline aqueous medium, wherein the reaction products RP either precipitate out of the solution as a solid or are isolated by evaporating the solution. The reaction products can also be prepared according to the literature method H. Möhrle et al, Pharmazie, 1999, 54(4), 269-279.

For the synthesis of the reaction products RP, molar ratios of Component B to the compound according to Formula (I) of about 1:1 to about 1:2 can be reasonable.

Particularly preferred reaction products RP are selected from compounds of Formulas (V), (VI) and (VII),

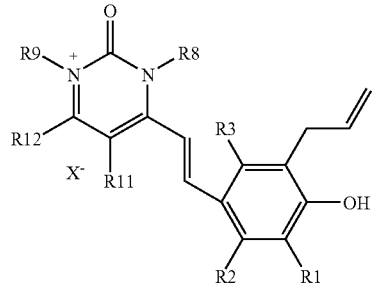

(V)

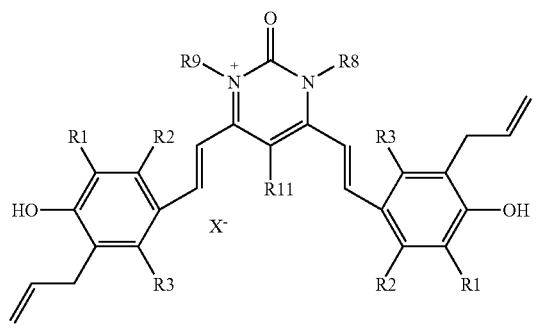

(VI)

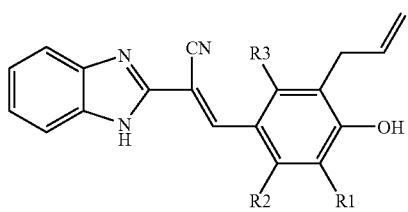

(VII)

in which the groups R1, R2, R3, R8, R9, R11, R12 and X⁻ are as previously defined for Formulas (I) and (II). All the previously cited embodiments of the above-mentioned groups are also applicable.

In Formula (V), R12 is quite particularly preferably a hydrogen atom.

The compounds of Formulas (V) and (VI) are preferred reaction products RP in accordance with the invention.

The above-mentioned compounds of Formula I, the compounds of Component B, Component C as well as the reaction products RP are preferably used in each case in an amount of 0.03 to 65 mmol, in particular, from 1 to 40 mmol, based on 100 g of the total colorant.

In addition, the inventive agents can comprise at least one developer component and optionally at least one coupler component as the oxidation dye precursors.

According to the invention, it may be preferred to use a p-phenylenediamine derivative or one of its physiologically compatible salts as the developer component. Particular preference is given to p-phenylenediamine derivatives of Formula (E1)

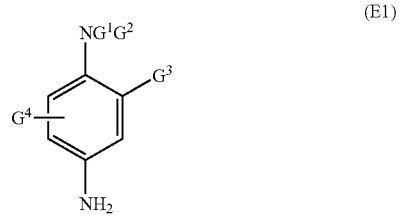

(E1)

wherein

G¹ is a hydrogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy ($C_1$- to $C_4$) alkyl group, a 4'-aminophenyl group or a $C_1$- to $C_4$ alkyl group that is substituted by a nitrogen-containing group, a phenyl group or a 4'-aminophenyl group;

G² is a hydrogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy ($C_1$- to $C_4$) alkyl group or a $C_1$- to $C_4$ alkyl group that is substituted by a nitrogen-containing group;

G³ is a hydrogen atom, a halogen atom, such as a chlorine, bromine, iodine or fluorine atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) hydroxyalkoxy group, a $C_1$- to $C_4$ acetylamino group, a $C_1$- to $C_4$ mesylamino alkoxy group or a $C_1$- to $C_4$ carbamoylamino alkoxy group;

G⁴ stands for a hydrogen atom, a halide atom or a $C_1$- to $C_4$ alkyl group or if G³ und G⁴ are in the ortho position relative to one another, they can together form a bridging a,ω-alkylenedioxo group, such as, for example, an ethylenedioxy group.

Examples of the $C_1$- to $C_4$ alkyl groups specified as substituents in the compounds according to the invention are the methyl, ethyl, propyl, isopropyl and butyl groups. Ethyl and methyl are preferred alkyl groups. Inventively preferred $C_1$- to $C_4$ alkoxy groups are a methoxy or ethoxy group, for example. Furthermore, preferred examples of a $C_1$- to $C_4$ hydroxyalkyl group that may be mentioned are a hydroxymethyl, a 2-hydroxyethyl, a 3-hydroxypropyl or a 4-hydroxybutyl group. A 2-hydroxyethyl group is particularly preferred. A particularly preferred $C_2$- to $C_4$ polyhydroxyalkyl group is the 1,2-dihydroxyethyl group. According to the invention, examples of halogen atoms are F, Cl or Br atoms, Cl atoms being quite particularly preferred. The other terms used are derived according to the invention from the definitions given here. Examples of nitrogen-containing groups of Formula (E1) are, in particular, the amino groups, $C_1$- to $C_4$ monoalkyl amino groups, $C_1$- to $C_4$ dialkylamino groups, $C_1$- to $C_4$ trialkyl amino groups, $C_1$- to $C_4$ monohydroxyalkyl amino groups, imidazolinium and ammonium.

Particularly preferred p-phenylenediamines of Formula (E1) are chosen from p-phenylenediamine, p-toluenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)-amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine and 5,8-diaminobenzo-1,4-dioxane, and their physiologically compatible salts.

According to the invention, quite particularly preferred p-phenylenediamine derivatives of Formula (E1) are p-phenylenediamine, p-toluenediamine, 2-(β-hydroxyethyl)-p-phenylenediamine, 2-(α,β-dihydroxyethyl)-p-phenylenediamine and N,N-bis-(β-hydroxyethyl)-p-phenylenediamine.

According to the invention, it may also be preferred to use compounds as the developer component, which comprise at least two aromatic nuclei that are substituted by amino and/or hydroxyl groups.

Among the binuclear developer components that can be used in the colorant compositions according to the invention, mention may be made, in particular, of the compounds which conform to the following Formula (E2), together with their physiologically compatible salts:

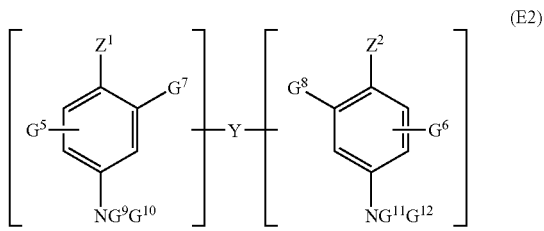 (E2)

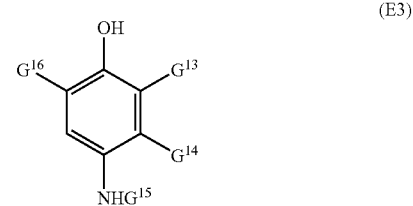 (E3)

wherein:
- $Z^1$ and $Z^2$, independently of one another, stand for a hydroxyl or $NH_2$ group, which is optionally substituted by a $C_1$- to $C_4$ alkyl group, by a $C_1$- to $C_4$ hydroxyalkyl group and/or by a bridge Y or which is optionally part of a bridging ring system,
- the bridge Y is an alkylene group having 1 to 14 carbon atoms, such as, for example, a linear or branched alkylene chain or an alkylene ring, which can be interrupted or terminated by one or more nitrogen-containing groups and/or one or more heteroatoms, such as oxygen, sulfur or nitrogen atoms and may possibly be substituted by one or more hydroxyl or $C_1$- to $C_8$ alkoxy groups, or a direct bond,
- $G^5$ und $G^6$, independently of one another, stand for a hydrogen or halogen atom, a $C_1$- to $C_4$ alkyl group, a $C_1$- to $C_4$ monohydroxyalkyl group, a $C_2$- to $C_4$ polyhydroxyalkyl group, a $C_1$- to $C_4$ amino alkyl group or a direct bond to the bridge Y,
- $G^7$, $G^8$, $G^9$, $G^{10}$, $G^{11}$ and $G^{12}$, independently of one another, are a hydrogen atom, a direct bond to the bridge Y or a $C_1$- to $C_4$ alkyl group, with the proviso that the compounds of Formula (E2) comprise only one bridge Y per molecule.

According to the invention, the substituents used in Formula (E2) are analogous to those defined in the above embodiments.

Preferred binuclear developer components of Formula (E2) are, in particular: N,N'-bis(β-hydroxyethyl)-N,N'-bis(4'-aminophenyl)-1,3-diaminopropane-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, bis(2-hydroxy-5-aminophenyl)methane, 1,3-bis(2,5-diaminophenoxy)propane-2-ol, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Quite particularly preferred binuclear developer components of Formula (E2) are N,N'-bis(β-hydroxyethyl)-N,N'-bis(4'-aminophenyl)-1,3-diaminopropane-2-ol, bis(2-hydroxy-5-aminophenyl)methane, 1,3-bis(2,5-diaminophenoxy)propane-2-ol, N,N'-bis(4'-aminophenyl)-1,4-diazacycloheptane and 1,10-bis(2,5-diaminophenyl)-1,4,7,10-tetraoxadecane or one of their physiologically compatible salts.

Moreover, according to the invention, it may be preferred to use a p-phenylenediamine derivative or one of its physiologically compatible salts as the developer component. p-Aminophenol derivatives of Formula (E3) are particularly preferred.

wherein:
- $G^{13}$ is a hydrogen atom, a halogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy ($C_1$- to $C_4$) alkyl group, a $C_1$- to $C_4$ aminoalkyl group, a hydroxy ($C_1$- to $C_4$) alkylamino group, a $C_1$- to $C_4$ hydroxyalkoxy group, a $C_1$- to $C_4$ hydroxyalkyl ($C_1$- to $C_4$) aminoalkyl group or a (di-$C_1$- to $C_4$ alkylamino) ($C_1$- to $C_4$) alkyl group, and
- $G^{14}$ is a hydrogen or halogen atom, a $C_1$- to $C_4$ alkyl group, a $C_1$- to $C_4$ monohydroxyalkyl group, a $C_2$- to $C_4$ polyhydroxyalkyl group, a ($C_1$- to $C_4$) alkoxy ($C_1$- to $C_4$) alkyl group, $C_1$- to $C_4$ amino alkyl group or a $C_1$- to $C_4$ cyanoalkyl group,
- $G^{15}$ stands for hydrogen, a $C_1$- to $C_4$ alkyl group, a $C_1$- to $C_4$ monohydroxyalkyl group, a $C_2$- to $C_4$ polyhydroxyalkyl group, a phenyl group or a benzyl group, and
- $G^{16}$ stands for hydrogen or a halogen atom.

According to the invention, the substituents in Formula (E3) are defined analogously to the above statements.

Preferred p-aminophenols of Formula (E3) are especially p-aminophenol, N-methyl-p-aminophenol, 4-amino-3-methyl-phenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol together with their physiologically compatible salts.

Quite particularly preferred compounds of Formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

Furthermore, the developer component can be selected from o-amino phenol and its derivatives, such as, for example 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazole-pyrimidine derivatives and their physiologically compatible salts.

Preferred pyridine derivatives are, in particular, the compounds which are described in the patents GB 1 026 978 and GB 1,153,196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in German Patent DE 2 359 399, the Japanese laid-open specification JP 02019576 A2 or in the laid-open specification WO 96/15765, such as 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP 740 931 and DE 195 43 988, such as 4,5-diamino-1-methylpyrazole, 4,5-diamino-1-(β-hydroxyethyl) pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl pyrazole, 4-amino-5-(2-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole.

Preferred pyrazolo pyrimidine derivatives are, in particular, the derivatives of the pyrazolo[1,5-a]pyrimidine of the following Formula (E4) and its tautomeric forms provided there exists a tautomeric equilibrium:

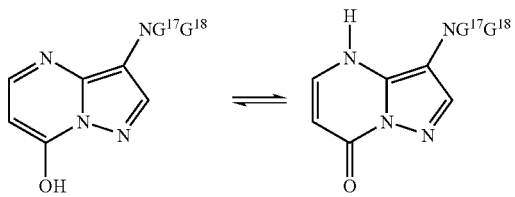

wherein:

$G^{17}$, $G^{18}$, $G^{19}$ and $G^{20}$ independently of one another stand for a hydrogen atom, a $C_1$- to $C_4$ alkyl group, an aryl group, a $C_1$- to $C_4$ hydroxyalkyl group, a $C_2$- to $C_4$ polyhydroxyalkyl group a ($C_1$- to $C_4$) alkoxy ($C_1$- to $C_4$) alkyl group, a $C_1$- to $C_4$ aminoalkyl group, optionally protected by an acetyl-ureido or a sulfonyl group, a ($C_1$- to $C_4$) alkylamino ($C_1$- to $C_4$) alkyl group, a di-[($C_1$- to $C_4$) alkyl] ($C_1$- to $C_4$) aminoalkyl group, wherein the dialkyl groups optionally form a carbocycle or a heterocycle with 5 or 6 chain members, a $C_1$- to $C_4$ hydroxyalkyl- or a di-($C_1$- to $C_4$) [hydroxyalkyl]-($C_1$- to $C_4$) aminoalkyl group, the X groups independently of one another stand for a hydrogen atom, a $C_1$-bis $C_4$ alkyl group, an aryl-group, a $C_1$- to $C_4$ hydroxyalkyl group, a $C_2$- to $C_4$ polyhydroxyalkyl group a ($C_1$- to $C_4$) alkoxy ($C_1$- to $C_4$) alkyl group, a $C_1$- to $C_4$ aminoalkyl group, a ($C_1$- to $C_4$) alkylamino ($C_1$- to $C_4$) alkyl group, a di-[($C_1$- to $C_4$) alkyl] ($C_1$- to $C_4$) aminoalkyl group, wherein the dialkyl groups optionally form a carbocycle or a heterocycle with 5 or 6 chain members, a $C_1$- to $C_4$ hydroxyalkyl- or a di-($C_1$- to $C_4$) [hydroxyalkyl] ($C_1$- to $C_4$) aminoalkyl group, an amino group, a $C_1$- to $C_4$ alkyl- or a di-($C_1$- to $C_4$) [hydroxyalkyl] ($C_1$- to $C_4$) amino group, a halogen atom, a carboxylic acid group or a sulfonic acid group.

i has the value 0, 1, 2 or 3,
p has the value 0 or 1,
q has the value 0 or 1 and
n has the value 0 or 1, with the proviso that
the sum of p+q is not equal to 0,
if p+q is equal to 2, then n has the value 0, and the groups $NG^{17}G^{18}$ and $NG^{19}G^{20}$ occupy the positions (2,3); (5,6); (6,7); (3,5) or (3,7);
if p+q is equal to 1, then n has the value 1, and the groups $NG^{17}G^{18}$ (or $NG^{19}G^{20}$) and the group OH occupy the positions (2,3); (5,6); (6,7); (3,5) or (3,7);

According to the invention, the substituents in Formula (E4) are defined analogously to the above statements.

If the pyrazolo[1,5-a]pyrimidine of the above Formula (E4) comprises a hydroxyl group in one of the positions 2, 5 or 7 of the ring system, there is a tautomeric equilibrium, which is illustrated, for example, in the following scheme:

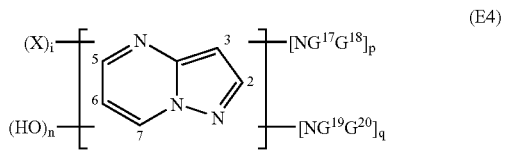

Among the pyrazolo[1,5-a]pyrimidines of the above Formula (E4), mention may be made in particular, of:

Pyrazolo[1,5-a]pyrimidine-3,7-diamine;
2,5-Dimethylpyrazolo[1,5-a]pyrimidine-3,7-diamine;
Pyrazolo[1,5-a]pyrimidine-3,5-diamine;
2,7-Dimethyl-pyrazolo[1,5-a]pyrimidine-3,5-diamine;
3-Aminopyrazolo[1,5-a]pyrimidine-7-ol;
3-Aminopyrazolo[1,5-a]pyrimidine-5-ol;
2-(3-Aminopyrazolo[1,5-a]pyrimidin-7-ylamino)ethanol;
2-(7-Aminopyrazolo[1,5-a]pyrimidin-3-ylamino)ethanol;
2-[(3-Aminopyrazolo[1,5-a]pyrimidin-7-yl)-(2-hydroxyethyl)amino]ethanol;
2-[(7-Aminopyrazolo[1,5-a]pyrimidin-3-yl)-(2-hydroxyethyl)amino]ethanol;
5,6-Dimethylpyrazolo[1,5-a]pyrimidine-3,7-diamine;
2,6-Dimethylpyrazolo[1,5-a]pyrimidine-3,7-diamine;
3-Amino-7-dimethylamino-2,5-dimethylpyrazolo[1,5-a]pyrimidine;

and their physiologically compatible salts and their tautomeric forms if a tautomeric equilibrium is present.

The pyrazolo[1,5-a]pyrimidines of the above Formula (E4) can be prepared as described in the literature by cyclization starting from an aminopyrazole or from hydrazine.

In a further preferred embodiment, the dyeing compositions according to the invention comprise at least one coupler component.

m-Phenylenediamine derivatives, naphthols, resorcinol and resorcinol derivatives, pyrazolones and m-amino phenol derivatives are generally used as the coupling components. Particularly suitable coupling substances are 1-naphthol, 1,5-, 2,7-, and 1,7-dihydroxynaphthalene, 5-amino-2-methylphenol, m-aminophenol, resorcinol, resorcinol monomethyl ether, m-phenylenediamine, 1-phenyl-3-methylpyrazolone-5, 2,2-Methyl-4-chlor-5-aminophenol-dichloro-3-aminophenol, 1,3-bis(2',4'-diaminophenoxy)propane, 2-chloro resorcinol, 4-chloro resorcinol, 2-chloro-6-methyl- 3-aminophenol, 2-amino-3-hydroxypyridine, 2-methyl resorcinol, 5-methyl resorcinol and 2-methyl-4-chloro-5-aminophenol.

According to the invention, preferred coupler components are m-Aminophenol and derivatives thereof such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-(ethylamino)-4-methylphenol and 2,4-dichloro-3-aminophenol, o-Aminophenol and derivatives thereof, m-Diaminobenzene and derivatives thereof such as, for example, 2,4-diaminophenoxyethanol, 1,3-bis-(2',4'-diaminophenoxy)propane, 1-methoxy-2-amino-4-(2'-hydroxyethylamino)benzene, 1,3-bis-(2',4'-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-[3-morpholin-4-ylphenyl)amino]ethanol, 3-amino-4-(2-methoxyethoxy)-5-methylphenylamine and 1-amino-3-bis-(2'-hydroxyethyl)aminobenzene, o-Diaminobenzene and derivatives thereof such as, for example, 3,4-diaminobenzoic acid and 2,3-diamino-1-methylbenzene, Di- and trihydroxybenzene derivatives such as, for example, resorcinol, resorcinol monomethyl ether, 2-methyl resorcinol, 5-methyl resorcinol, 2,5-dimethyl resorcinol, 2-chloro resorcinol, 4-chloro resorcinol, pyrogallol and 1,2,4-trihydroxybenzene, Pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, Naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, Morpholine derivatives such as, for example, 6-hydroxybenzomorpholine and 6-aminobenzomorpholine, Quinoxaline derivatives such as, for example, 6-methyl-1,2,3,4-tetrahydroquinoxaline, Pyrazole derivatives such as, for example, 1-phenyl-3-methylpyrazol-5-one, Indole derivatives such as, for example, 4-hydroxyindole, 6-hydroxyindole and 7-hydroxyindole, Pyrimidine derivatives, such as, for example 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine, or Methylenedioxybenzene derivatives such as, for example, 1-hydroxy-3,4-methylenedioxybenzene, 1-amino-3,4-methylenedioxybenzene and 1-(2'-hydroxyethyl)amino-3,4-methylenedioxybenzene as well as their physiologically compatible salts.

According to the invention, particularly preferred coupler components are 1-naphthol, 1,5-, 2,7- and 1,7-dihydroxynaphthalene, 3-aminophenol, 5-amino-2-methylphenol, 2-amino-3-hydroxypyridine, resorcinol, 4-chloro resorcinol, 2-chloro-6-methyl-3-aminophenol, 2-methyl resorcinol, 5-methyl resorcinol, 2,5-dimethyl resorcinol and 2,6-dihydroxy-3,4-dimethylpyridine.

Furthermore, in the context of a fifth embodiment, the precursors of nature-analogous dyes that are used in the inventive agents are preferably those indoles and indolines, which have at least one hydroxyl or amino group, preferably as the substituent on the 6-membered ring. These groups can carry further substituents, e.g., in the form of an etherified or esterified hydroxyl group or an alkylated amino group. In a second preferred embodiment, the colorants comprise at least one indole- or indoline derivative.

Derivatives of 5,6-dihydroxyindoline of Formula VIIIa are particularly well suited as the precursors of nature-analogous hair dyes,

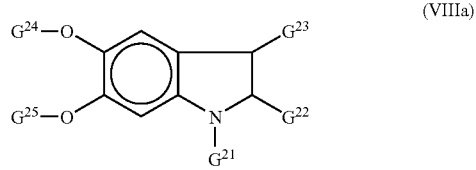

(VIIIa)

in which, independently of one another $G^{21}$ stands for hydrogen, a $C_1$-$C_4$ alkyl group or a $C_1$-$C_4$ hydroxyalkyl group, $G^{22}$ stands for hydrogen or a —COOH group, wherein the —COOH group may also be present as the salt with a physiologically compatible cation, $G^{23}$ stands for hydrogen or a $C_1$-$C_4$ alkyl group, $G^{24}$ stands for hydrogen, a $C_1$-$C_4$ alkyl group or a —CO—$G^{26}$ group, in which $G^{26}$ stands for a $C_1$-$C_4$ alkyl group, and $G^{25}$ stands for one of the groups cited for $G^{24}$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, emphasis is placed particularly on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

In addition, derivatives of 5,6-hydroxyindole of Formula VIIIb are exceptionally suitable as precursors of nature-analogous hair dyes,

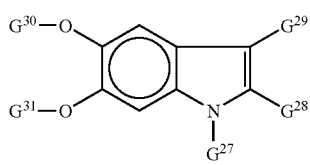

(VIIIb)

in which, independently of one another
- $G^{27}$ stands for hydrogen, a $C_1$-$C_4$ alkyl group or a $C_1$-$C_4$ hydroxyalkyl group,
- $G^{23}$ stands for hydrogen or a —COOH group, wherein the —COOH group may also be present as the salt with a physiologically compatible cation,
- $G^{29}$ stands for hydrogen or a $C_1$-$C_4$ alkyl group,
- $G^{30}$ stands for hydrogen, a $C_1$-$C_4$ alkyl group or a —CO—$G^{32}$ group, in which $G^{32}$ stands for a $C_1$-$C_4$ alkyl group, and
- $G^{31}$ stands for one of the groups cited for $G^{30}$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is given to N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives can be employed in the inventive colorants both as free bases and also in the form of their physiologically compatible salts of inorganic or organic acids, e.g., the hydrochlorides, the sulfates and hydrobromides. The indole or indoline derivatives are comprised in these, usually in amounts of 0.05-10% by weight, preferably 0.2-5% by weight.

The presence of oxidizing agents, e.g., $H_2O_2$, can be dispensed with, particularly when the inventive agent does not comprise any oxidation dye precursors. If the inventive agent comprises air-oxidizable oxidation dye precursors or indole- or indoline derivatives, then in this case there is no problem with dispensing with oxidizing agents. However, in certain cases hydrogen peroxide or other oxidizing agents can be added to the inventive agent in order to produce nuances that are lighter than the keratinic fibers being dyed. Generally, oxidizing agents are employed in an amount of 0.01 to 6 wt. %, based on the application solution. A preferred oxidizing agent for human hair is $H_2O_2$. Mixtures of a plurality of oxidizing agents, such as for example a combination of hydrogen peroxide and peroxydisulfates of the alkali metals and alkaline earth metals or sources of iodine ions, such as e.g., alkali metal iodides and hydrogen peroxide or the above-mentioned peroxydisulfates, can also be used. According to the invention, the oxidizing agent or the combination of oxidizing agents together with oxidation catalysts can be used in the hair colorant. Oxidation catalysts are for example metal salts, metal chelate complexes or metal oxides, which permit an easy change between two oxidation states of the metal ions. Examples are salts, chelate complexes or oxides of iron, ruthenium, manganese and copper. Enzymes illustrate further possible oxidation catalysts. Suitable enzymes are, for example, peroxidases, which can considerably enhance the effect of small amounts of hydrogen peroxide. Those enzymes that directly oxidize the oxidation dye precursors with the help of atmospheric oxygen are further inventively suitable, such as, for example, the laccases, or those which produce small amounts of hydrogen peroxide in situ and in so doing biocatalytically activate the oxidation of the dye precursors. Particularly suitable catalysts for the oxidation of the dye precursors are the so-called 2-electron oxidoreductases in combination with the substrates specific therefor, e.g.,

- pyranose oxidase and e.g., D-glucose or galactose,
- glucose oxidase and D-glucose,
- glycerine oxidase and glycerine,
- pyruvate oxidase and pyruvic acid or its salts,
- alcohol oxidase and alcohol (MeOH, EtOH),
- lactate oxidase and lactic acid or its salts,
- tyrosinase oxidase and tyrosine,
- uricase and uric acid or its salts,
- choline oxidase and choline,
- amino acid oxidase and amino acids.

In a sixth embodiment, in order to further modify the color nuances, the inventive colorants comprise, in addition to the inventively comprised compounds, further conventional substantive dyes, such as nitrophenylenediamine, nitroaminophenols, azo dyes, anthraquinones or indophenols. Preferred substantive dyestuffs are the compounds with the international designations or tradenames HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57: 1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 as well as 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene.

In addition, the inventive agents can preferably comprise a cationic substantive dye. Particular preference is given hereto (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) substantive dyes, which comprise a heterocycle that has at least one quaternary nitrogen atom, as are specified, for example, in the claims 6 to 11 of EP A2 998 908, which is explicitly incorporated here by reference.

Preferred cationic substantive dyes of group (c) are, in particular, the following compounds:

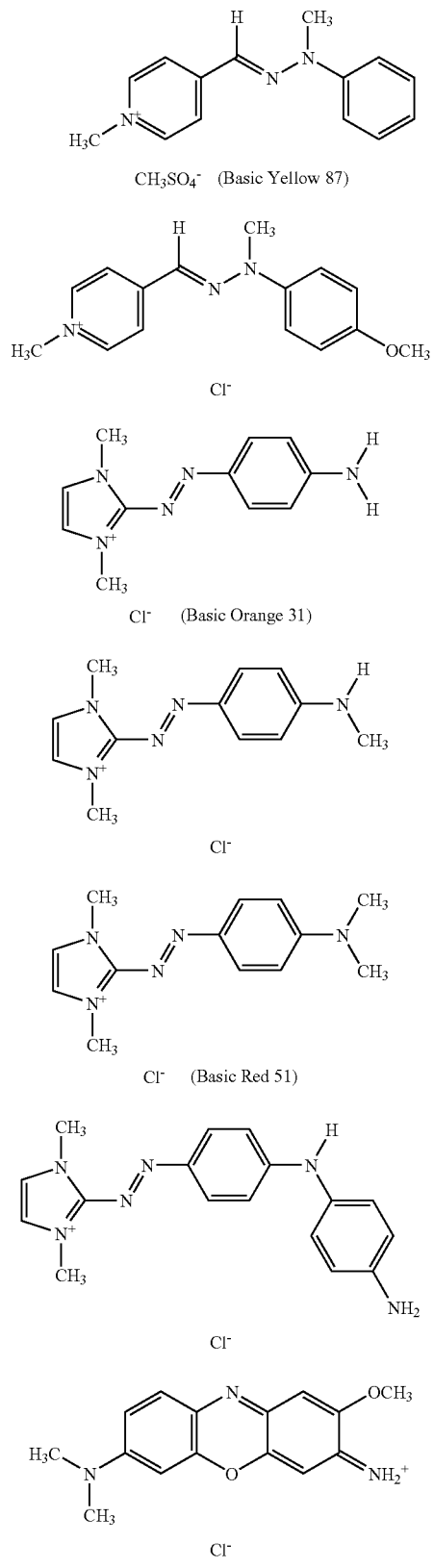

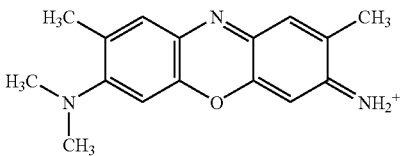

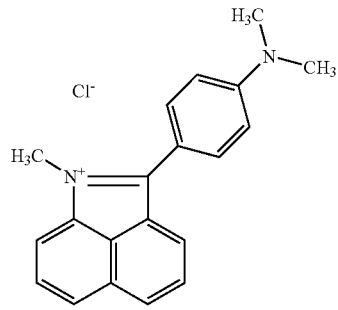

The compounds corresponding to Formulas (DZ1), (DZ3) and (DZ5) are quite particularly preferred cationic substantive dyes of group (c). According to the invention, the cationic substantive dyes that are commercialized under the tradename Arianor®, are particularly preferred cationic substantive dyes.

The inventive agents according to this embodiment comprise the substantive dyes preferably in a quantity of 0.01 to 20 wt. %, based on the total colorant.

In addition, the inventive preparations can also comprise naturally occurring dyestuffs as are for example comprised in henna red, henna neutral, henna black, camomile leaves, sandalwood, black tea, alder buckthorn bark, sage, logwood, madder root, cashew, cedar and alkanet root.

It is not required that each of the optionally comprised substantive dyestuffs be pure compounds. In fact, the inventive colorants, due to the manufacturing processes for the individual dyestuffs, may comprise minor quantities of even more components, in so far as they have no detrimental influence on the coloration result or that they must be excluded on other grounds, e.g., toxicological grounds.

To obtain additional and more intensive colorations, the inventive agents can comprise additional color reinforcers. The color reinforcers are preferably selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, their derivatives and their physiologically compatible salts.

Each of the above-mentioned color reinforcers can be added in an amount of 0.03 to 10 wt. %, particularly 0.5 to 5 wt. %, each based on 100 g of the ready-for-use colorant.

The pH of the inventive agents can be pH 4 to 12, preferably pH 5 to 10.

The inventive colorants furnish intensive colorations already at physiologically compatible temperatures of below 45° C. In consequence, they are particularly suitable for dyeing human hair. Usually, for use on human hair, the colorants can be incorporated into an aqueous cosmetic carrier. Suitable aqueous cosmetic carriers are, for example, creams, emulsions, gels or also surfactant-containing foaming solutions, such as, for example, shampoos or other preparations that are suitable for use on the keratinic fibers. If necessary, the colorants can also be incorporated into anhydrous carriers. Examples of further suitable and inventively preferred ingredients are given below.

According to the invention, an otherwise customary carrier for agents for dyeing human hair is especially employed as the cosmetic carrier. The inventive dyes can be formulated, apart from the inventive components, with suitably known dyes or comprise typical ingredients for them. Examples of further suitable and inventively preferred ingredients are given below.

The inventive agents preferably comprise the compounds of Formula (I) and the compounds of component B in a suitable aqueous, alcoholic or aqueous alcoholic carrier. For the purposes of dyeing the hair, such carriers are, for example, creams, emulsions, gels and also surfactant-containing foaming solutions, such as, for example, shampoos, foam aerosols or other preparations that are suitable for use on the hair. However, it is also conceivable to incorporate the dyestuff precursors into a powdered or tablet-shaped formulation.

For the purposes of the present invention, aqueous-alcoholic solutions are understood as meaning aqueous solutions comprising 3 to 70% by weight of a $C_1$-$C_4$ alcohol, in particular, ethanol or isopropanol. The compositions according to the invention can additionally comprise further organic solvents, such as, for example, methoxybutanol, benzyl alcohol, ethyl diglycol or 1,2-propylene glycol. Preference here is given to all water-soluble organic solvents.

In many cases the dyes comprise at least one surfactant, wherein, in principal, not only anionic, but also zwitterionic, ampholytic, nonionic and cationic surfactants are suitable. However, in many cases it has proved advantageous to select the surfactants from among anionic, zwitterionic or nonionic surfactants.

Suitable anionic surfactants for the inventive preparations are all anionic surface-active materials that are suitable for use on the human body. They are characterized by a water solubilizing anionic group, such as e.g., a carboxylate, sulfate, sulfonate or phosphate group and a lipophilic alkyl group containing about 10 to 22 carbon atoms. In addition, the molecule may comprise glycol or polyglycol ether groups, ester, ether and amide groups as well as hydroxyl groups. Exemplary suitable anionic surfactants are, each in the form of the sodium, potassium and ammonium salts as well as the mono-, di- and trialkanol ammonium salts with 2 or 3 carbon atoms in the alkanol group, linear fatty acids containing 10 to 22 carbon atoms (soaps),
ether carboxylic acids of the formula R—O—($CH_2$—$CH_2O$)$_x$—$CH_2$—COOH, in which R is a linear alkyl group with 10 to 22 carbon atoms and x=0 or 1 to 16,
acyl sarcosides with 10 to 18 carbon atoms in the acyl group,
acyl taurides with 10 to 18 carbon atoms in the acyl group,
acyl isethionates with 10 to 18 carbon atoms in the acyl group,
sulfosuccinic acid mono- and dialkyl esters with 8 to 18 carbon atoms in the alkyl group and sulfosuccinic acid mono-alkyl polyoxyethyl esters with 8 to 18 carbon atoms in the alkyl group and 1 to 6 oxyethylene groups,
linear alkane sulfonates with 12 to 18 carbon atoms,
linear alpha-olefin sulfonates with 12 to 18 carbon atoms
alpha-sulfo fatty acid methyl esters of fatty acids with 12 to 18 carbon atoms,
alkyl sulfates and alkyl polyglycol ether sulfates of formula R—O($CH_2$—$CH_2O$)$_x$—$SO_3H$, in which R is preferably a linear alkyl group with 10 to 18 carbon atoms and x=0 or 1 to 12,
mixtures of surface-active hydroxy sulfonates according to DE-A-37 25 030,
sulfated hydroxyalkyl polyethylene- and/or hydroxyalkylene propylene glycol ethers according to DE-A-37 23 354,
sulfonated unsaturated fatty acids containing 12 to 24 carbon atoms and 1 to 6 double bonds according to DE-A-39 26 344,
esters of tartaric acid and citric acid with alcohols that represent the addition products of about 2 to 15 molecules of ethylene oxide and/or propylene oxide on fatty alcohols containing 8 to 22 carbon atoms.

Preferred anionic surfactants are alkyl sulfates, alkyl polyglycol ether sulfates and ether carboxylic acids with 10 to 18 carbon atoms in the alkyl group and up to 12 glycol ether groups in the molecule, and especially salts of saturated and particularly unsaturated $C_8$-$C_{22}$ carboxylic acids, such as oleic acid, stearic acid, isostearic acid and palmitic acid.

Zwitterionic surfactants are designated as those surface-active compounds that carry at least one quaternary ammonium group and at least one —COO$^{(-)}$ or —SO$_3^{(-)}$ group in the molecule. Particularly suitable zwitterionic surfactants are the so-called betaines such as the N-alkyl-N,N-dimethyl ammonium glycinates, for example the cocoalkyl dimethyl ammonium glycinate, N-acylaminopropyl-N,N-dimethyl ammonium glycinates, for example the cocoacylaminopropyl dimethyl ammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative, known under the CTFA name cocoamidopropyl betaine.

The ampholytic surfactants are understood to include such surface-active compounds that apart from a $C_{8-18}$ alkyl or acyl group, comprise at least one free amino group and at least one —COOH or —SO$_3$H group in the molecule, and are able to form internal salts. Examples of suitable ampholytic surfactants are N-alkylglycines, N-alkylamino propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 18 carbon atoms in the alkyl group. Particularly preferred ampholytic surfactants are N-cocoalkylamino propionate, the cocoacylaminoethylamino propionate and the $C_{12-18}$ acyl sarcosines.

Nonionic surfactants comprise e.g., a polyol group, a polyalkylene glycol ether group or a combination of polyol and polyglycol ether groups as the hydrophilic group. Exemplary compounds of this type are Addition products of 2 to 30 moles ethylene oxide and/or 0 to 5 moles propylene oxide to linear fatty alcohols with 8 to 22 carbon atoms, to fatty acids with 12 to 22 carbon atoms and to alkyl phenols with 8 to 15 carbon atoms in the alkyl group,
$C_{12-22}$ fatty acid mono and diesters of addition products of 1 to 30 moles ethylene oxide on glycerine;
$C_{8-22}$ alkyl mono- and oligoglycosides and their ethoxylated analogs,
Addition products of 5 to 60 moles ethylene oxide on castor oil and hydrogenated castor oil,
Addition products of ethylene oxide on sorbitan fatty acid esters Addition products of ethylene oxide on fatty acid alkanolamides.

Examples of the cationic surfactants that can be used in the inventive hair treatment agents are especially quaternary ammonium compounds. Ammonium halides such as alkyl trimethyl ammonium chlorides, dialkyl dimethyl ammonium chlorides and trialkyl methyl ammonium chloride are preferred, e.g., cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. The quaternized protein hydrolyzates illustrate further inventively usable cationic surfactants.

Cationic silicone oils, such as, for example, the commercially available products Q2-7224 (manufacturer: Dow Corning; a stabilized trimethylsilylamodimethicone), Dow Corning 929 emulsion (comprising a hydroxylamino modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80) are similarly suitable according to the invention.

Alkylamido amines, particularly fatty acid amido amines such as stearylamidopropyldimethylamine, available under the name Tego Amid®S 18, are characterized by a good conditioning action, especially by their good biodegradability.

Quaternary ester compounds, so called "esterquats," such as methyl hydroxyalkyl dialkoyloxyalkyl ammonium methosulfates, commercialized under the trade name Stepantex®, also possess very good biodegradability.

An example of a suitable cationic surfactant quaternary sugar derivative is the commercial product Glucquat® 100, a "lauryl methyl gluceth-10 hydroxypropyl dimonium chloride" according to CFTA nomenclature.

For compounds with alkyl groups that are used as surfactants, they may each be pure substances. However, it is normally preferred to start with natural vegetal or animal raw materials for the manufacture of these materials, with the result that mixtures of substances are obtained, which have different alkyl chain lengths that depend on each raw material.

For surfactants, which are represented by the addition products of ethylene oxide and/or propylene oxide to fatty alcohols or derivatives of these addition products, both products with a "normal" homolog distribution as well as those with a narrow homolog distribution may be used. The term "normal" homolog distribution is understood to mean mixtures of homologs obtained from the reaction of fatty alcohols and alkylene oxide using alkali metals, alkali metal hydroxides or alkali metal alcoholates as catalysts. On the other hand, narrow homolog distributions are obtained if e.g., hydrotalcite, alkaline earth metal salts of ether carboxylic acids, alkaline earth metal oxides, hydroxides or alcoholates are used as catalysts. The use of products with a narrow homolog distribution can be preferred.

Further exemplary active products, auxiliaries and additives are nonionic polymers, such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes with quaternary groups, dimethyl diallyl ammonium chloride polymers, acrylamide-dimethyl diallyl ammonium chloride copolymers, dimethylaminoethyl methacrylate-vinyl pyrrolidone copolymers quaternized with diethyl sulfate, vinyl pyrrolidone-imidazolinium methochloride copolymers and quaternized polyvinyl alcohol, zwitterionic and amphoteric polymers, such as, for example, acrylamidopropyl trimethyl ammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners like agar-agar, guar gum, alginates, xanthane gum, gum arabica, karaya gum, locust bean flour, linseed gums, dextrans, cellulose derivatives, e.g., methyl cellulose, hydroxyalkyl cellulose and carboxymethyl cellulose, starch fractions and derivatives of amylose, amylopectin and dextrins, clays such as e.g., bentonite or synthetic hydrocolloids such as e.g., polyvinyl alcohol, structurants such as glucose and maleic acid, hair conditioning compounds like phospholipids, for example, soya lecithin, egg lecithin and cephalin, as well as silicone oils, protein hydrolyzates, particularly those of elastin, collagen, keratin, milk protein, soya protein and wheat protein, their condensation products with fatty acids as well as quaternized protein hydrolyzates, perfume oils, dimethyl isosorbitol and cyclodextrins, solubilizers, such as ethanol, isopropanol, ethylene glycol, propylene glycol, glycerine and diethylene glycol, anti-dandruff active materials like Piroctone Olamine and Zinc Omadine, additional substances for adjusting the pH, such as ammonia, monoethanolamine, basic amino acids and citric acid active ingredients, such as panthenol, pantothenic acid, allantoin, pyrrolidone carboxylic acids and salts thereof, plant extracts and vitamins, cholesterol, UV stabilizers, thickeners like sugar esters, polyol esters or polyol alkyl ethers, fats and waxes like spermaceti, beeswax, montan wax, paraffins, fatty alcohols and fatty acid esters, fatty acid alkanolamides, chelating agents like EDTA, NTA and phosphonic acids, swelling and penetration agents such as glycerol, propylene glycol monoethyl ether, carbonates, hydrogen carbonates, guanidines, ureas, and primary, secondary and tertiary phosphates, imidazoles, tannins, pyrrole, opacifiers like latex, pearlizers like ethylene glycol mono and distearate, blowing agents like propane-butane mixtures, $N_2O$, dimethyl ether, $CO_2$ and air, as well as antioxidants.

The ingredients of the aqueous carrier are added in the usual amounts for the purpose of manufacturing the inventive colorant, e.g., emulsifiers are added in concentrations of 0.5 to 30 wt. % and thickeners in concentrations of 0.1 to 25 wt. % of the total colorant.

For the color result it can be advantageous to add ammonium or metal salts to the colorants. Suitable metal salts are e.g., formates, carbonates, halides, sulfates, butyrates, valeriates, capronates, acetates, lactates, glycolates, tartrates, citrates, gluconates, propionates, phosphates and phosphonates of alkali metals, like potassium, sodium or lithium, alkaline earth metals, such as magnesium, calcium, strontium or barium, or of aluminum, manganese, iron, cobalt, copper or zinc, wherein sodium acetate, lithium bromide, calcium bromide, calcium gluconate, zinc chloride, zinc sulfate, magnesium chloride, magnesium sulfate, ammonium carbonate, -chloride and -acetate are preferred. These salts are preferably comprised in an amount of 0.03 to 10 wt. %, particularly 0.5 to 5 wt. %, based on 100 g of the total ready-for-use colorant.

The pH of the ready-for-use color preparations is normally between 2 and 11, preferably between 5 and 10.

A second subject matter of the present invention relates to the use of at least one compound corresponding to Formula I,

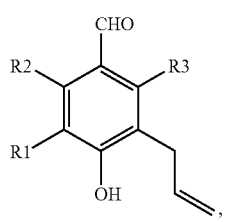

(I)

in which R1, R2 and R3 are defined as in the first subject matter of the invention, together with at least one CH-acidic compound as Component B, as the coloring component in hair dyes.

In a preferred embodiment, those compounds corresponding to Formula I, which are selected from the preferred and particularly preferred representatives cited in the first subject matter of the invention, are used as the coloring component in hair dyes.

Moreover, it can be preferred to use at least one reaction product RP from a compound corresponding to Formula I and a representative of Component B as the coloring component in hair dyes.

A third subject matter of the present invention relates to a method for dyeing fibers containing keratin, especially human hair, in which a colorant, comprising in a cosmetic carrier at least one compound according to Formula I as Component A,

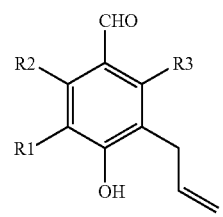

(I)

in which R1, R2 and R3 are defined as in the first subject matter of the invention, together with at least one CH-acidic compound as Component B is applied onto the keratin-containing fibers, left for a time, usually about 15-30 minutes on the fibers, and then rinsed out again or washed out with a shampoo. During the contact time of the agent with the fibers, it can be advantageous to support the coloring process by supplying heat. The supply of heat can be from a heat source, such as e.g., warm air from a stream of warm air, as also, especially for a hair coloration on living subjects, from the body temperature of the subject. For the latter alternative, the areas being dyed are normally covered with a cap.

Accordingly, the compounds corresponding to Formula I and the compounds of Component B, particularly their preferred and particularly preferred representatives cited above, are applied as the coloring components either simultaneously onto the hair or else consecutively, i.e., in a multi-step method, wherein it is irrelevant which component is applied first. The optionally comprised ammonium or metal salts can be added to the compounds of Formula I or to the compounds of Component B. There can be an interval of up to 30 minutes between the addition of the individual components. A pre-treatment of the fibers with the salt solution is also possible.

Before using the inventive agent in the inventive method, it can be desirable to subject the keratin-containing fibers being dyed to a pre-treatment. The time sequence for the required pre-treatment step and the application of the inventive agent does not have to be immediately one after the other, rather the interval between the pre-treatment step and the application of the inventive agent can be up to two weeks at most. There are many methods of pre-treatment. Preferably, the fiber is subjected to V1 bleaching prior to the application of the inventive agent or V2 oxidative coloration prior to the application of the inventive agent.

In the context of the pre-treatment V1, the keratin-containing fiber is treated with a hair bleaching composition. In addition to an oxidizing agent, such as hydrogen peroxide, the hair bleaching composition preferably comprises at least one inorganic peroxy salt that acts as the oxidation and bleach booster, such as e.g., a peroxysulfate of sodium, potassium or ammonium. Colorations according to the inventive method acquire a particular brilliance and color depth as a result of the pre-treatment V1.

In the context of the pre-treatment V2, an agent comprising the above-mentioned oxidation dye precursors as the developer components and optional coupler components as well as optional above-mentioned derivatives of indole or indoline, is applied onto the fiber, and after a contact time, optionally with the addition of above-mentioned oxidizing agents on the hair, is left for 5-45 minutes on the keratin fiber. The hair is then rinsed. The existing oxidation colorations can be given a new color nuance by the subsequent application of the inventive agent. By choosing the color nuance of the inventive agent in the same color nuance of the oxidative coloration, then the coloration of the existing oxidation coloration can be refreshed in accordance with the inventive method. It can be seen that the color refreshing or nuancing according to the inventive method is superior in color brilliance and color depth to a color refreshing or nuancing effected solely with conventional substantive dyes.

If in addition to the compounds according to Formula I and the compounds of Component B, the hair dye comprises hydrogen peroxide as the oxidizing agent or a hydrogen peroxide-containing oxidizing agent mixture, then the pH of the hydrogen peroxide-containing hair dye is preferably in a pH range of pH 7 to pH 11, preferably pH 8 to pH 10. The oxidizing agent can be mixed with the hair dye immediately prior to use and applied to the hair. If the compounds of Formula I and Component B are to be applied in a two-step method onto the hair, then the oxidizing agent is used in one of the two steps with the corresponding dyeing component.

For this purpose, it can be preferred to package the oxidizing agent with one of the dye components in one container.

The compounds according to Formula I and the compounds of Component B can be stored either in separate containers or together in one container, either in a liquid to pasty preparation (aqueous or anhydrous) or as a solid, for example as a dry powder. If the components are stored together in a liquid preparation then they should be essentially anhydrous and have an acid pH in order to diminish any reaction of the components. If the components are stored together, then it is preferred to present them as solids, in particular, in the form of a preferably multi-layer molded body, e.g., as a tablet. In the case of multi-layered molded bodies, Component A is incorporated into one layer and Component B into another, wherein a further layer preferably lies between the layers as the separation layer. The separation layer is free of compounds of Components A and B. When stored separately, the reactive components are first intimately blended together immediately prior to use. With dry storage, a defined quantity of warm (30° C. to 80° C.) water is normally added before use to prepare a homogeneous mixture.

A fourth subject matter of the invention is the use of
at least one compound according to Formula (I),

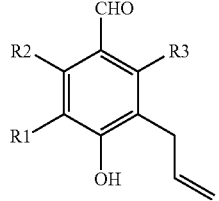
(I)

in which R1, R2 and R3 are defined as in the first subject matter of the invention, together with
at least one CH-acidic compound as Component B, for nuancing oxidation colorations of keratin-containing fibers, especially human hair. For use, it is irrelevant whether the nuancing is carried out simultaneously with the oxidative coloration or the oxidative coloration is done before the nuancing.

A fifth subject matter of the invention is the use of
at least one compound according to Formula (I), (I)

in which R1, R2 and R3 are defined as in the first subject matter of the invention, together with
at least one CH-acidic compound as Component B, for the color refreshment of keratin-containing fibers that were dyed with oxidative dyes.

The colorations of keratin-containing fibers are known to be exposed to environmental influences, such as light, rubbing or washing and can thus lose their brilliance and color depth. In the worst of cases a shift in the nuance of the coloration sometimes occurs. Such changed colorations of keratin-containing fibers can be shifted back, when desired, by a color refreshment to the approximate color state present immediately after the original coloration. According to the invention, a combination of at least one compound of Formula I and at least one compound of Component B is used for such a color refreshment.

EXAMPLES

Synthetic Examples

Synthetic Example 1

Preparation of 3-allyl-4-hydroxybenzaldehyde (A1)

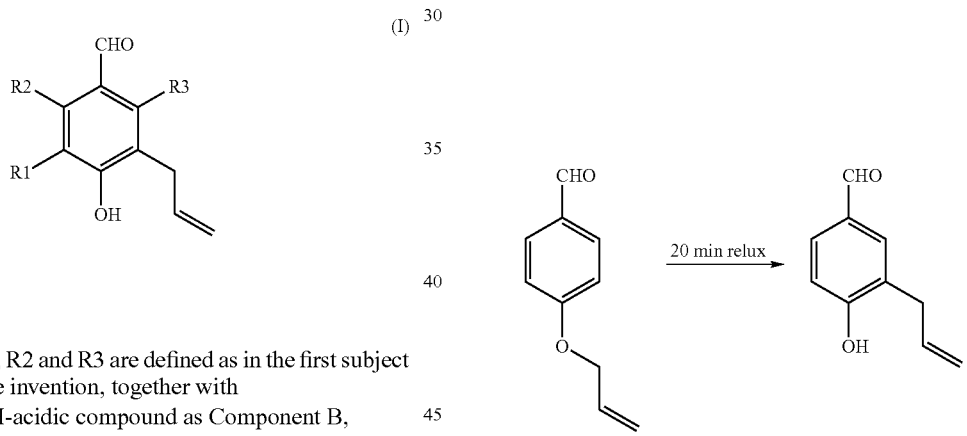

Allyloxybenzaldehyde (10.0 g, 0.062 mol) in 200 ml diphenyl ether was heated under reflux for 20 minutes. After cooling the reaction mixture, 200 ml of chloroform were added and the mixture was extracted with 200 ml 2N sodium hydroxide. The aqueous extracts were washed with chloroform and then acidified under cooling with concentrated hydrochloric acid. The resulting precipitate was exhaustively extracted with chloroform. The organic phase was dried over magnesium sulfate and concentrated.

Yield: 10.0 g (100%)

M. pt.: 47-57° C.

$^1$H-NMR (400 MHz, CDCl$_3$): δ [ppm]=3.48 (d, 2H); 5.12-5.21 (2×dd, 2H); 5.94-6.18 (m, 1H); 6.81 (br, OH); 6.98 (d, 1H); 7.70 (d, 1H); 7.75 (s, 1H); 9.91 (s, 1H)

Synthetic Example 2

Step 1: Preparation of 3-methoxy-4-(2-propenyloxy)benzaldehyde

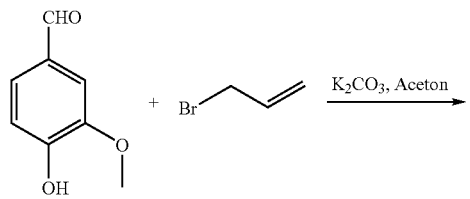

Vanillin (20.0 g, 0.130 mol) and allyl bromide (19.9 g, 0.160 mol) were heated under reflux together with potassium carbonate (27.3 g, 0.200 mol) in 150 ml acetone (abs.) for 8 hours. After cooling, the solid was filtered off and washed with acetone. A yellow oil was obtained after a thorough concentration of the organic phases.

Yield: 26.5 g (100%)

$^1$H-NMR (400 MHz, CDCl$_3$): δ [ppm]=3.93 (s, 3H); 4.68 (d, 2H); 5.31-5.38 (dd, 1H); 5.40-5.49 (dd, 1H); 6.00-6.14 (m, 1H); 6.95 (d, 1H); 7.41 (s, 1H); 7.46 (d, 1H); 9.85 (s, 1H);

Step 2: Preparation of 3-allyl-4-hydroxy-5-methoxybenzaldehyde (A2)

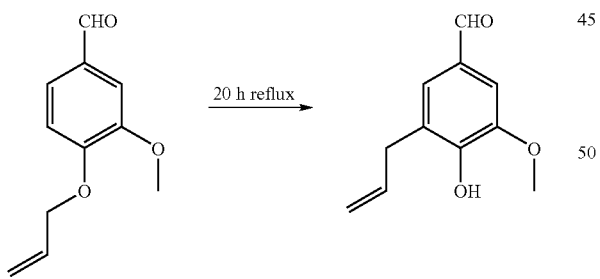

3-Methoxy-4-(2-propenyloxy)benzaldehyde (19.7 g, 0.100 mol) was heated under reflux in 75 ml mesitylene (1,3,5-trimethylbenzene) for 20 hours. After cooling, 250 ml 2N sodium hydroxide were added to the reaction mixture. The aqueous phase was washed two times with diethyl ether. The aqueous phase was subsequently acidified with concentrated hydrochloric acid under ice cooling and then extracted with ethyl acetate. After drying and concentrating the organic phase, there remained a light orange-colored oil that crystallized on cooling.

Yield: 7.2 g (37%)

M. pt.: 81-82° C.

$^1$H-NMR (400 MHz, CDCl$_3$): δ [ppm]=3.47 (d, 2H); 3.98 (s, 3H); 5.01-5.12 (dd, 1H); 5.17-5.28 (dd, 1H); 5.99-6.09 (m, 1H); 6.32 (br, OH); 7.32 (s, 2H); 9.80 (s, 1H).

Synthetic Example 3

Step 1: Preparation of 3-ethoxy-4-(2-propenyloxy)benzaldehyde

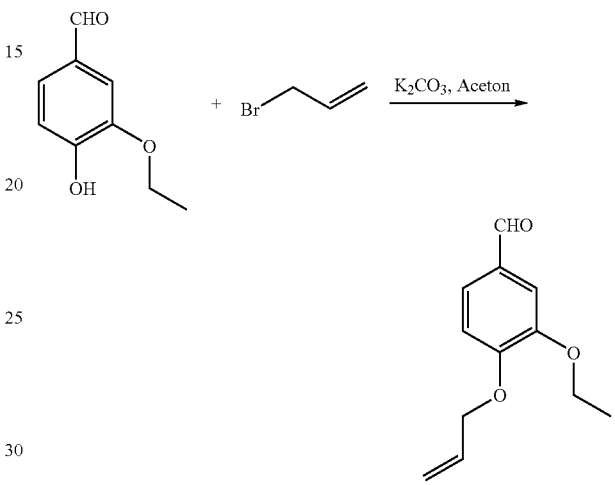

Ethyl vanillin (21.6 g, 0.130 mol) and allyl bromide (19.9 g, 0.160 mol) were heated under reflux together with potassium carbonate (27.3 g, 0.200 mol) in 150 ml acetone (abs.) for 8 hours. After cooling, the solid was filtered off and washed with acetone. A yellow oil was obtained after a thorough concentration of the organic phases.

Yield: 21.7 g (72%)

$^1$H-NMR (400 MHz, CDCl$_3$): δ [ppm]=1.49 (t, 3H); 4.18 (q, 2H); 4.72 (d, 2H); 5.30-5.35 (dd, 1H); 5.41-5.46 (dd, 1H); 6.00-6.11 (m, 1H); 6.95 (d, 1H); 7.40 (d, 1H); 7.43 (s, 1H); 9.87 (s, 1H)

Step 2: Preparation of 3-allyl-4-hydroxybenzaldehyde (A3)

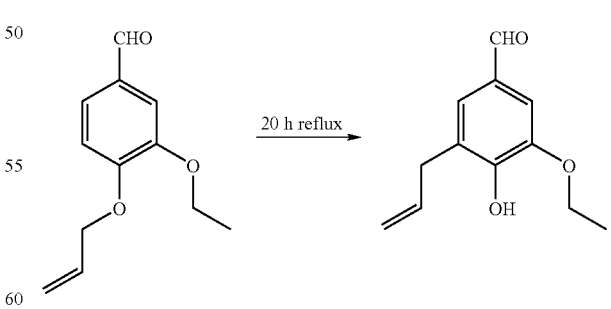

3-Ethoxy-4-(2-propenyloxy)benzaldehyde (20.0 g, 0.087 mol) was heated under reflux in 75 ml mesitylene (1,3,5-trimethylbenzene) for 20 hours. After cooling, 250 ml 2N sodium hydroxide were added to the reaction mixture. The aqueous phase was washed two times with diethyl ether. The aqueous phase was subsequently acidified with concentrated hydrochloric acid under ice cooling and then extracted with ethyl acetate. After drying and concentrating the organic phase, there remained a light orange-colored oil that crystallized on cooling.

Yield: 9.2 g (57%)

M. pt.: 45° C.

$^1$H-NMR (400 MHz, CDCl$_3$): δ [ppm]=1.46 (t, 3H); 3.47 (d, 2H); 4.19 (q, 2H); 5.10-5.18 (2×dd, 2H); 5.81-6.02 (m, 1H); 6.23 (br, OH); 7.30 (s, 2H); 9.81 (s, 1H)

Synthetic Example 4

Preparation of
3-allyl-4-hydroxy-5-methylbenzaldehyde (A4)

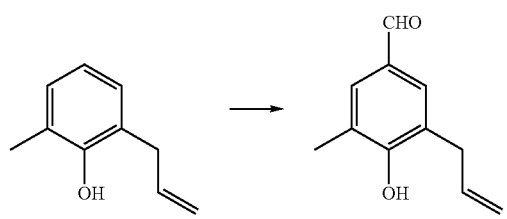

2-Allyl-6-methylphenol (7.6 g, 0.051 mol) and urotropin (hexamethylenetetramine, 11.9 g, 0.085 mol) were heated under reflux in 50 ml of 50% conc. acetic acid for 4½ hours. Subsequently, 56 ml of half-concentrated hydrochloric acid were then added to the hot reaction solution. The solution was heated under reflux for a further half hour. After cooling to room temperature, the precipitated solid was filtered off, washed with a little water and dried at room temperature under vacuum.

Yield: 9.0 g (100%)

$^1$H-NMR (400 MHz, DMSO-d$_6$): δ [ppm]=2.24 (s, 3H); 3.38 (d, 2H); 5.01-5.11 (2×dd, 2H); 6.02 (m, 1H); 7.47 (s, 1H); 7.53 (s, 1H); 9.48 (s, 1H); 9.75 (s, 1H)

Synthetic Example 5

Step 1: Preparation of
3-bromo-4-(2-propenyloxy)benzaldehyde

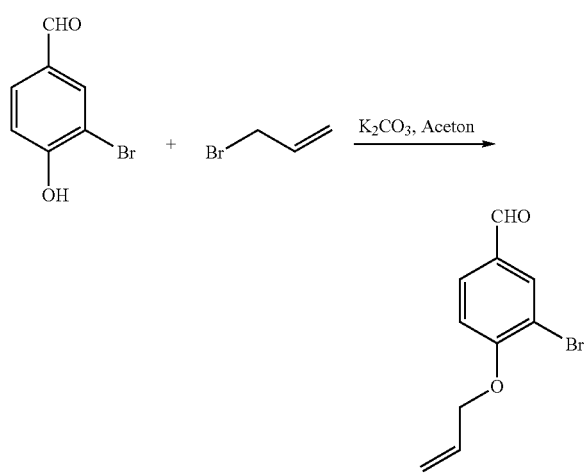

3-Bromo-4-hydroxybenzaldehyde (20.1 g, 0.100 mol) and allyl bromide (14.5 g, 0.120 mol) were heated under reflux together with potassium carbonate (20.7 g, 0.150 mol) in 150 ml acetone (abs.) for 8 hours. After cooling, the solid was filtered off and washed with acetone. After complete concentration of the organic phase, there was obtained an oily residue that was used directly in the second step without further purification.

Yield: 23.7 g (93%)

$^1$H-NMR (400 MHz, DMSO-d$_6$): δ [ppm]=4.81 (d, 2H); 5.28-5.31 (dd, 1H); 5.49-5.53 (dd, 1H); 6.03-6.18 (m, 1H); 7.27 (d, 1H); 7.91 (d, 1H); 8.11 (s, 1H); 9.89 (s, 1H).

Step 2: Preparation of
3-allyl-5-bromo-4-hydroxybenzaldehyde (A5)

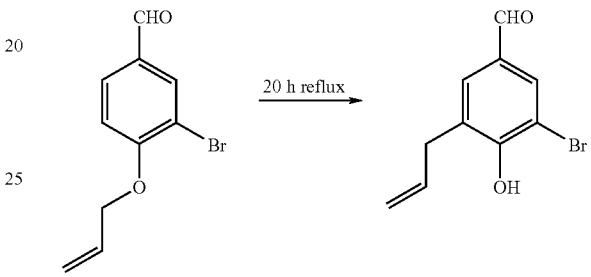

3-Bromo-4-(2-propenyloxy)benzaldehyde (20.0 g, 0.083 mol) was heated under reflux in 75 ml mesitylene (1,3,5-trimethylbenzene) for 20 hours. After cooling, 250 ml 2N sodium hydroxide were added to the reaction mixture. The aqueous phase was washed two times with diethyl ether. The aqueous phase was subsequently acidified with concentrated hydrochloric acid under ice cooling and then extracted with ethyl acetate. After drying and concentrating the organic phase, there remained an oil that crystallized on cooling.

Yield: 2.2 g (11%)

$^1$H-NMR (400 MHz, DMSO-d$_6$): δ [ppm]=3.45 (d, 2H); 5.01-5.15 (2×dd, 2H); 5.96-6.11 (m, 1H); 7.68 (s, 1H); 8.14 (s, 1H); 9.80 (s, 1H)

Dyeing Examples

Manufacture of a Dye

Aqueous Gel Formulation for Component A Gel 1.

| | |
|---|---|
| Aromatic aldehyde (Component A) | 10 mmol |
| Natrosol HR 250 | 2 g |
| NaOH (50% aqueous solution) | optionally a few drops |
| Water, deionized | ad 100 g |

Aqueous Gel formulation for Component B Gel 2

| | |
|---|---|
| CH-acidic compound (Component B) | 10 mmol |
| Natrosol HR 250 | 2 g |
| Water, deionized | ad 100 g |

The aromatic aldehyde (Component A) was dissolved or suspended in a little water. When needed, the solubility was increased by alkalization with a few drops of 50% sodium hydroxide solution. Subsequently, water was added to make up 98 g and stirring was continued until complete dissolution of the aldehyde (with partial gentle heating to ca. 40° C.). Finally, the Natrosol was added with stirring and the swelling process awaited.

The CH-acidic compound (Component B) was first dissolved in a little water with stirring and then made up to 98 g with water. The Natrosol was added with stirring and the swelling process awaited.

Both of the gel formulations (Gel 1 and Gel 2) were mixed in the weight ratio 1:1, and then the pH was adjusted with ammonia or tartaric acid.

The resulting ready-for use hair dye was applied on a strand of 90% grayed, unpretreated human hair (liquid weight ratio gel mixture to hair=2:1) and evenly dispersed with an applicette. After a contact time of 30 minutes at 32° C., the strand was rinsed out with lukewarm water and then dried in a stream of warm air. The colorations were visually assessed under a daylight lamp. The result is summarized in Table 1.

TABLE 1

| Component A | Component B | pH | Color result |
|---|---|---|---|
| A1 | B1 | 9 | bright violet red |
| A1 | B2 | 9 | bright violet red |
| A1 | B3 | 9 | bright violet red |
| A1 | B4 | 9 | lemon yellow |
| A2 | B1 | 9 | intense violet |
| A2 | B2 | 9 | intense violet |
| A2 | B3 | 9 | intense violet |
| A2 | B4 | 9 | intense yellow |
| A3 | B1 | 9 | pale violet |
| A3 | B2 | 9 | pale violet |
| A3 | B3 | 9 | pale violet |
| A3 | B4 | 9 | yellow |
| A4 | B1 | 9 | intense violet |
| A4 | B2 | 9 | intense violet |
| A4 | B3 | 9 | bright violet |
| A4 | B4 | 9 | bright lemon yellow |
| A5 | B1 | 9 | red violet |
| A5 | B2 | 9 | intense red violet |
| A5 | B3 | 9 | red violet |
| A5 | B4 | 9 | bright yellow |

A1 3-Allyl-4-hydroxybenzaldehyde
A2 3-Allyl-4-hydroxy-5-methoxybenzaldehyde
A3 3-Allyl-5-ethoxy-4-hydroxybenzaldehyde
A4 3-Allyl-4-hydroxy-5-methylbenzaldehyde
A5 3-Allyl-5-bromo-4-hydroxybenzaldehyde
B1 1,2-Dihydro-1,3,4,6-tetramethyl-2-oxopyrimidinium hydrogen sulfate
B2 1-Allyl-1,2-dihydro-3,4,6-trimethyl-2-oxopyrimidinium bromide
B3 1,2-Dihydro-1-(2-hydroxyethyl)-3,4,6-trimethyl-2-oxopyrimidinium p-toluenesulfonate
B4 2-(Cyanomethyl)benzimidazole

The invention claimed is:

1. An agent for dyeing keratin-containing fibers, especially human hair, comprising a cosmetic carrier, and
(A) at least one compound of Formula I,

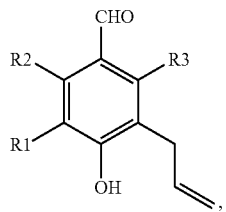

(I)

wherein each of $R^1$, $R^2$ and $R^3$ is independently a hydrogen atom, a halogen atom, a $C_1$-$C_6$ alkyl group, a $C_2$-$C_6$ alkenyl group, a hydroxyl group, a $C_1$-$C_6$ alkoxy group, a $C_1$-$C_6$ hydroxyalkyl group, a $C_2$-$C_6$ polyhydroxyalkyl group, a hydroxy $C_1$-$C_6$ alkyloxy group, a sulfonyl group, a carboxyl group, a $C_1$-$C_6$ alkoxycarbonyl group, a hydroxy $C_2$-$C_6$ alkyloxycarbonyl group, a sulfonic acid group, a sulfonamido group, a sulfonamide group, a $C_2$-$C_6$ acyl group, a formyl group, a nitro group, a carbamoyl group —C(O)—$NR^4R^5$, or a —$(CH_2)_n NR^6R^7$ group wherein each of $R^4$, $R^5$, $R^6$ and $R^7$ is independently a hydrogen atom, a $C_1$-$C_6$ alkyl group or a $C_2$-$C_6$ hydroxyalkyl group; and n is number from 0 to 6, wherein $R^1$ and $R^2$ can form a 5- or 6-membered aromatic or heteroaromatic ring; and (B) at least one CH-acidic compound.

2. The agent of claim 1 wherein $R^2$ and $R^3$ is a hydrogen atom.

3. The agent of claim 1 wherein the group $R^1$ is a hydrogen atom, a $C_1$-$C_6$ alkyl group, a $C_2$-$C_6$ alkenyl group, a $C_1$-$C_6$ alkoxy group, a formyl group, a hydroxyl group, a halogen atom, a carboxy group or a nitro group.

4. The agent of claim 1 wherein the compound of Formula I is selected from the group consisting of:
3-Allyl-4-hydroxybenzaldehyde,
3-Allyl-4-hydroxy-5-methoxybenzaldehyde,
3-Allyl-5-ethoxy-4-hydroxybenzaldehyde,
3-Allyl-4-hydroxy-5-methyl benzaldehyde,
3-Allyl-5-bromo-4-hydroxybenzaldehyde,
3,5-Diallyl-4-hydroxybenzaldehyde,
3-Allyl-4,5-dihydroxybenzaldehyde,
3-Allyl-4-hydroxy-5-nitrobenzaldehyde,
3-Allyl-5-carboxy-4-hydroxybenzaldehyde (3-allyl-5-formyl-2-hydroxybenzoic acid),
3-Allyl-4-hydroxy-5-formylbenzaldehyde (5-allyl-4-hydroxyisophthalaldehyde).

5. The agent of claim 1 wherein Component (B) is selected from the group consisting of a compound of Formula (II) and/or Formula (III)

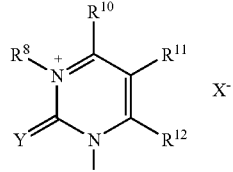

(II)

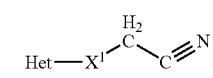

(III)

wherein each of $R^8$ and $R^9$ is independently a linear or cyclic $C_1$-$C_6$ alkyl group, a $C_2$-$C_6$ alkenyl group, an optionally substituted aryl group, an optionally substituted heteroaryl group, an aryl $C_1$-$C_6$ alkyl group, a $C_1$-$C_6$ hydroxyalkyl group, a $C_2$-$C_6$ polyhydroxyalkyl group, a $C_1$-$C_6$ alkoxy $C_1$-$C_6$ alkyl group, a $R^IR^{II}N$—$(CH_2)_m$— group, wherein each of $R^I$ and $R^{II}$ is independently a hydrogen atom, a $C_1$-$C_4$ alkyl group, a $C_1$-$C_4$ hydroxyalkyl group or an aryl $C_1$-$C_6$ alkyl group, wherein $R^I$ and $R^{II}$ together with the nitrogen atom can form a 5-, 6- or 7-membered ring and m stands for a number 2, 3, 4, 5 or 6, each of $R^{10}$ and $R^{12}$ is independently a hydrogen atom or a $C_1$-$C_6$ alkyl group, wherein at least one of the groups $R^{10}$ and $R^{12}$ id a $C_1$-$C_6$ alkyl group, $R^{11}$ is a hydrogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, a group $R^{III}R^{IV}N$—$(CH_2)_q$—, wherein each of $R^{III}$ and $R^{IV}$ is independently a hydrogen atom, a $C_1$-$C_6$ alkyl group, a $C_1$-$C_6$ hydroxyalkyl group or an aryl $C_1$-$C_6$ alkyl group and q is 1, 2, 3, 4, 5 or 6, wherein the group $R^{11}$ together with one of the groups $R^{10}$ or $R^{12}$ can form a 5- or 6-membered aromatic ring that can be optionally substituted with a halogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, a nitro group, a hydroxy group, a group $R^V R^{VI} N$—$(CH_2)_s$—, wherein each of $R^V$ and $R^{VI}$ is independently a hydrogen atom, a $C_1$-$C_6$ alkyl group, a $C_1$-$C_6$ hydroxyalkyl group or an aryl $C_1$-$C_6$ alkyl group and is 0, 1, 2, 3, 4, 5 or 6; Y is an oxygen atom, a sulfur atom or $NR^{VII}$, wherein $R^{VII}$ is a hydrogen atom, an aryl group, a heteroaryl group, a $C_1$-$C_6$ alkyl group or a $C_1$-$C_6$ arylalkyl group; $X^-$ is a physiologically compatible anion; Het stands for an optionally substituted heteroaromatic group; $X^1$ is a direct bond or a carbonyl group.

6. The agent of claim 1 wherein Component (B) is 1H-benzimidazol-2-ylacetonitrile [2-(cyanomethyl)benzimidazole] and wherein the agent further comprising a salt is selected from the group consisting of
  1,2-Dihydro-1,3,4,6-tetramethyl-2-oxo-pyrimidinium,
  1,2-Dihydro-1,3-diethyl-4,6-dimethyl-2-oxo-pyrimidinium,
  1,2-Dihydro-1,3-dipropyl-4,6-dimethyl-2-oxo-pyrimidinium,
  1,2-Dihydro-1,3-di(2-hydroxyethyl)-4,6-dimethyl-2-oxo-pyrimidinium,
  1,2-Dihydro-1,3-diphenyl-4,6-dimethyl-2-oxo-pyrimidinium,
  1,2-Dihydro-1,3,4-trimethyl-2-oxo-pyrimidinium,
  1,2-Dihydro-1,3-diethyl-4-methyl-2-oxo-pyrimidinium,
  1,2-Dihydro-1,3-dipropyl-4-methyl-2-oxo-pyrimidinium,
  1,2-Dihydro-1,3-di(2-hydroxyethyl)-4-methyl-2-oxo-pyrimidinium,
  1,2-Dihydro-1,3-diphenyl-4-methyl-2-oxo-pyrimidinium,
  1-Allyl-1,2-dihydro-3,4,6-trimethyl-2-oxo-pyrimidinium,
  1,2-Dihydro-1-(2-hydroxyethyl)-3,4,6-trimethyl-2-oxo-pyrimidinium,
  1,2-Dihydro-1,3,4,6-tetramethyl-2-thioxo-pyrimidinium,
  1,2-Dihydro-1,3-diethyl-4,6-dimethyl-2-thioxo-pyrimidinium,
  1,2-Dihydro-1,3,dipropyl,4-6-dimethyl-2-thioxo-pyrimidinium
  1,2-Dihydro-1,3-di(2-hydroxyethyl)-4,6-dimethyl-2-thioxo-pyrimidinium,
  1,2-Dihydro-1,3-diphenyl-4,6-dimethyl-2-thioxo-pyrimidinium,
  1,2-Dihydro-1,3,4-trimethyl-2-thioxo-pyrimidinium,
  1,2-Dihydro-1,3-diethyl-4-methyl-2-thioxo-pyrimidinium,
  1,2-Dihydro-1,3-dipropyl-4-methyl-2-thioxo-pyrimidinium,
  1,2-Dihydro-1,3-di(2-hydroxyethyl)-4-methyl-2-thioxo-pyrimidinium,
  1,2-Dihydro-1,3-diphenyl-4-methyl-2-thioxo-pyrimidinium,
  1,2-Dihydro-3,4-dimethyl-2-oxo-quinazolinium and
  1,2-Dihydro-3,4-dimethyl-2-thioxo-quinazolinium or a combination thereof wherein the anion of the salt is a physiologically compatible counter ion $X^-$.

7. The agent of claim 1 further comprising at least one reactive carbonyl compound as Component (C) selected from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxy-benzaldehyde, 4-hydroxy-2,6-dimethoxy-benzaldehyde, 4-hydroxy-2-methyl-benzaldehyde, 4-hydroxy-2,3-dimethyl-benzaldehyde, 4-hydroxy-2,5-dimethyl-benzaldehyde, 4-hydroxy-2,6-dimethyl-benzaldehyde, 3,5-diethoxy-4-hydroxy-benzaldehyde, 2,6-diethoxy-4-hydroxy-benzaldehyde, 3-hydroxy-4-methoxy-benzaldehyde, 2-hydroxy-4-methoxy-benzaldehyde, 2-ethoxy-4-hydroxy-benzaldehyde, 3-ethoxy-4-hydroxy-benzaldehyde, 4-ethoxy-2-hydroxy-benzaldehyde, 4-ethoxy-3-hydroxy-benzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methyl-benzaldehyde, 2,4-dihydroxy-5-methyl-benzaldehyde, 2,4-dihydroxy-6-methyl-benzaldehyde, 2,4-dihydroxy-3-methoxy-benzaldehyde, 2,4-dihydroxy-5-methoxy-benzaldehyde, 2,4-dihydroxy-6-methoxy-benzaldehyde, 2,5-dihydroxybenzaldehyde, 2,6-dihydroxybenzaldehyde, 3,4-dihydroxybenzaldehyde, 3,4-dihydroxy-2-methyl-benzaldehyde, 3,4-dihydroxy-5-methyl-benzaldehyde, 3,4-dihydroxy-6-methyl-benzaldehyde, 3,4-dihydroxy-2-methoxy-benzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodo-benzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 4-nitro-1-naphthaldehyde, 2-nitrocinnamaldehyde, 3-nitrocinnamaldehyde, 4-nitrocinnamaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylamino-cinnamaldehyde, 4-dibutylamino-benzaldehyde, 4-diphenylamino-benzaldehyde, 4-(1-imidazolyl)-benzaldehyde and piperonal.

8. The agent of claim 1 wherein the amount of each of the compounds of Formula I, the compounds of Component B, and optionally the compounds of Component C is from 0.03 to 65 mmol based on 100 g of the total colorant.

9. The agent of claim 8 wherein the amount is from 1 to 40 mmol, based on 100 g of the total colorant.

10. The agent of claim 1 further comprising color reinforcers selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine and mixtures thereof.

11. The agent of claim 1 further comprising from 0.01 to 6 wt. % of an oxidizing agents based on the application solution.

12. The agent of claim 11 wherein the oxidizing agent is $H_2O_2$.

13. The agent of claim 1 further comprising at least one developer component as an oxidation dye precursor and optionally at least one coupler component.

14. The agent of claim 1 further comprising at least one substantive dye.

15. The agent of claim 14 the amount of the substantive dye is from 0.01 to 20 wt. % based on the total colorant.

16. The agent of claim 1 further comprising anionic, zwitterionic or non-ionic surfactants.

17. A hair dye comprising a coloration component comprising a compound of Formula I as recited in claim 1 and a compound of Component (B) as recited in claim 1.

18. A method for dyeing keratin-containing fibers, especially human hair, comprising the steps of (a) contacting the hair with a composition comprising an agent of claim 1 and a cosmetic ingredient for about 15-30 minutes, and (b) removing the composition by rinsing.

19. The method of claim 18 wherein the composition is removed by washing with a shampoo.

20. The method of claim 18 wherein the keratin-containing fibers are bleached or colored with an oxidation colorant before step (a).

21. A compound of Formula (V)

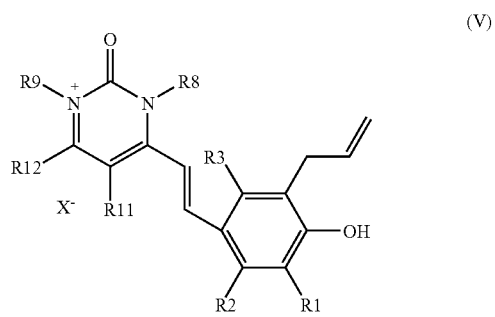

wherein $R^1$, $R^2$, $R^3$, $R^8$, $R^9$, $R^{11}$, $R^{12}$ and $X^-$ are the same as defined in claim 5.

22. A compound of Formula (VI)

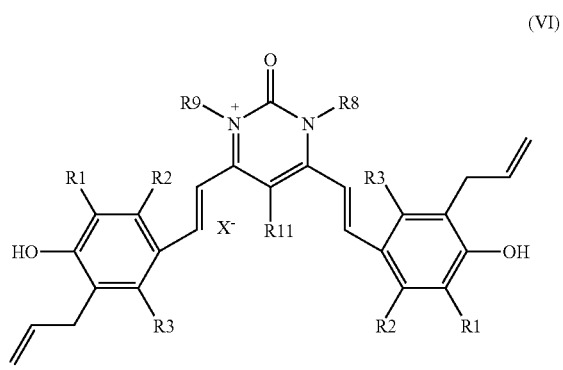

wherein $R^1$, $R^2$, $R^3$, $R^8$, $R^9$, $R^{11}$ and $X^-$ are the same as defined in claim 5.

* * * * *